United States Patent
Aghassian et al.

(10) Patent No.: US 10,530,179 B2
(45) Date of Patent: *Jan. 7, 2020

(54) EXTERNAL CONTROLLER FOR AN IMPLANTABLE MEDICAL DEVICE SYSTEM WITH AN EXTERNAL CHARGING COIL POWERED BY AN EXTERNAL BATTERY

(71) Applicant: Boston Scientific Neuromodulation Corporation, Valencia, CA (US)

(72) Inventors: Daniel Aghassian, Glendale, CA (US); Terril G. Lewis, Spring, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 15/896,985

(22) Filed: Feb. 14, 2018

(65) Prior Publication Data
US 2018/0175658 A1   Jun. 21, 2018

Related U.S. Application Data

(63) Continuation of application No. 14/826,050, filed on Aug. 13, 2015, now Pat. No. 9,929,584.
(Continued)

(51) Int. Cl.
*H02J 7/02* (2016.01)
*H02J 7/00* (2006.01)
(Continued)

(52) U.S. Cl.
CPC ............ *H02J 7/025* (2013.01); *A61N 1/3787* (2013.01); *A61N 1/37229* (2013.01);
(Continued)

(58) Field of Classification Search
CPC .. H02J 7/025; H02J 50/80; H02J 50/12; H02J 5/005; H02J 7/0042; H02J 7/0054;
(Continued)

(56) References Cited

U.S. PATENT DOCUMENTS

| 4,561,443 A | 12/1985 | Hogrefe et al. |
| 5,314,457 A | 5/1994 | Jeutter |

(Continued)

FOREIGN PATENT DOCUMENTS

| JP | 2004-73725 | 3/2004 |
| WO | 2005/032658 | 4/2005 |
| WO | 2007/124325 | 11/2007 |

OTHER PUBLICATIONS

Medtronic, Inc.'s Restore™ Rechargeable Neurostimulation System, as described in Applicant's Information Disclose Statement filed herewith.
(Continued)

*Primary Examiner* — Drew A Dunn
*Assistant Examiner* — Sailesh Thapa
(74) *Attorney, Agent, or Firm* — Lewis & Reese, PLLC

(57) ABSTRACT

An integrated external controller/charger system for an implantable medical device is disclosed comprising an external controller/charger device with a Graphical User Interface (GUI) and first battery, and an external charging coil assembly coupleable to the external controller/charger device and including or associated with a second battery. The second battery is used to energize a charging coil in the external charging coil assembly, while the first battery is used to power other aspects of the system (data telemetry circuitry, control circuitry, the GUI, etc.). Because the second battery powers the relatively high-power charging function, the first battery in the external controller/charger device can be made smaller. Additionally, the second battery enables a suitable external controller device (e.g. a mobile device such as a cell phone) to provide charging functionality even if its first battery is otherwise inadequate.

20 Claims, 14 Drawing Sheets

Related U.S. Application Data

(60) Provisional application No. 62/072,737, filed on Oct. 30, 2014.

(51) Int. Cl.
  *H04B 5/00* (2006.01)
  *H02J 50/12* (2016.01)
  *H02J 50/80* (2016.01)
  *H02J 5/00* (2016.01)
  *A61N 1/378* (2006.01)
  *A61N 1/372* (2006.01)

(52) U.S. Cl.
  CPC ............ *H02J 5/005* (2013.01); *H02J 7/0042* (2013.01); *H02J 7/0047* (2013.01); *H02J 7/0054* (2013.01); *H02J 50/12* (2016.02); *H02J 50/80* (2016.02); *H04B 5/0037* (2013.01); *H02J 2007/0096* (2013.01); *H04B 5/0081* (2013.01)

(58) Field of Classification Search
  CPC ...... H02J 7/027; H02J 7/04; H02J 2007/0096; A61N 1/37229; A61N 1/3787; H04B 5/0037; H04B 5/0081
  See application file for complete search history.

(56) References Cited

U.S. PATENT DOCUMENTS

| | | |
|---|---|---|
| 5,948,006 A | 9/1999 | Mann |
| 6,275,737 B1 | 8/2001 | Mann |
| 6,505,077 B1 | 1/2003 | Kast |
| 6,516,227 B1 | 2/2003 | Meadows |
| 6,553,263 B1 | 4/2003 | Meadows |
| 6,658,300 B2 | 12/2003 | Govari |
| 7,177,698 B2 | 2/2007 | Klosterman et al. |
| 7,200,504 B1 | 4/2007 | Fister |
| 7,286,880 B2 | 10/2007 | Olson et al. |
| 7,428,438 B2 | 9/2008 | Parramon et al. |
| 8,335,569 B2 | 12/2012 | Aghassian |
| 8,463,392 B2 | 6/2013 | Aghassian |
| 8,498,716 B2 | 7/2013 | Chen et al. |
| 8,588,925 B2 | 11/2013 | Carbunaru et al. |
| 8,682,444 B2 | 3/2014 | Aghassian et al. |
| 9,186,518 B2 | 11/2015 | Kothandaraman |
| 9,327,135 B2 | 5/2016 | Vansickle et al. |
| 9,339,660 B2 | 5/2016 | Feldman et al. |
| 9,533,162 B2 | 1/2017 | Ter-Petrosyan et al. |
| 9,929,584 B2 * | 3/2018 | Aghassian .............. H02J 7/025 |
| 2003/0078634 A1 | 4/2003 | Schulman et al. |
| 2004/0098068 A1 | 5/2004 | Carbunaru et al. |
| 2005/0021108 A1 | 1/2005 | Klosterman et al. |
| 2005/0088357 A1 | 4/2005 | Hess et al. |
| 2005/0113887 A1 | 5/2005 | Bauhahn |
| 2005/0143781 A1 | 6/2005 | Carbunaru et al. |
| 2005/0187590 A1 | 8/2005 | Boveja et al. |
| 2005/0245971 A1 | 11/2005 | Brockway et al. |
| 2007/0060967 A1 | 3/2007 | Strother et al. |
| 2007/0060980 A1 | 3/2007 | Strother et al. |
| 2007/0270921 A1 | 11/2007 | Strother et al. |
| 2008/0027513 A1 | 1/2008 | Carbunaru |
| 2009/0069869 A1 | 3/2009 | Stouffer et al. |
| 2009/0082835 A1 | 3/2009 | Jaax et al. |
| 2009/0112291 A1 | 4/2009 | Wahlstrand et al. |
| 2009/0118796 A1 * | 5/2009 | Chen ................. A61N 1/37229 607/60 |
| 2010/0204756 A1 | 8/2010 | Aghassian |
| 2011/0004278 A1 | 1/2011 | Aghassian |
| 2011/0071597 A1 | 3/2011 | Aghassian |
| 2011/0166630 A1 | 7/2011 | Phillips et al. |
| 2011/0260681 A1 | 10/2011 | Guccione et al. |
| 2012/0012630 A1 | 1/2012 | Lui et al. |
| 2012/0101551 A1 | 4/2012 | Aghassian et al. |
| 2013/0096651 A1 | 4/2013 | Ozawa et al. |
| 2013/0123881 A1 * | 5/2013 | Aghassian ........... A61N 1/3787 607/61 |
| 2014/0025140 A1 | 1/2014 | Lui et al. |
| 2014/0114373 A1 | 4/2014 | Aghassian |
| 2015/0015195 A1 | 1/2015 | Leabman et al. |
| 2015/0015196 A1 | 1/2015 | Ormesher et al. |
| 2015/0360038 A1 | 12/2015 | Zottola et al. |

OTHER PUBLICATIONS

Advanced Neuromodulation Systems (ANS), Inc. EON™ Neurostimulation Systems IPG, as described in Applicant's Information Disclosure Statement filed herewith.
International Search Report and Written Opinion regarding corresponding PCT Application No. PCT/US2015/045290, dated Nov. 19, 2015.

\* cited by examiner

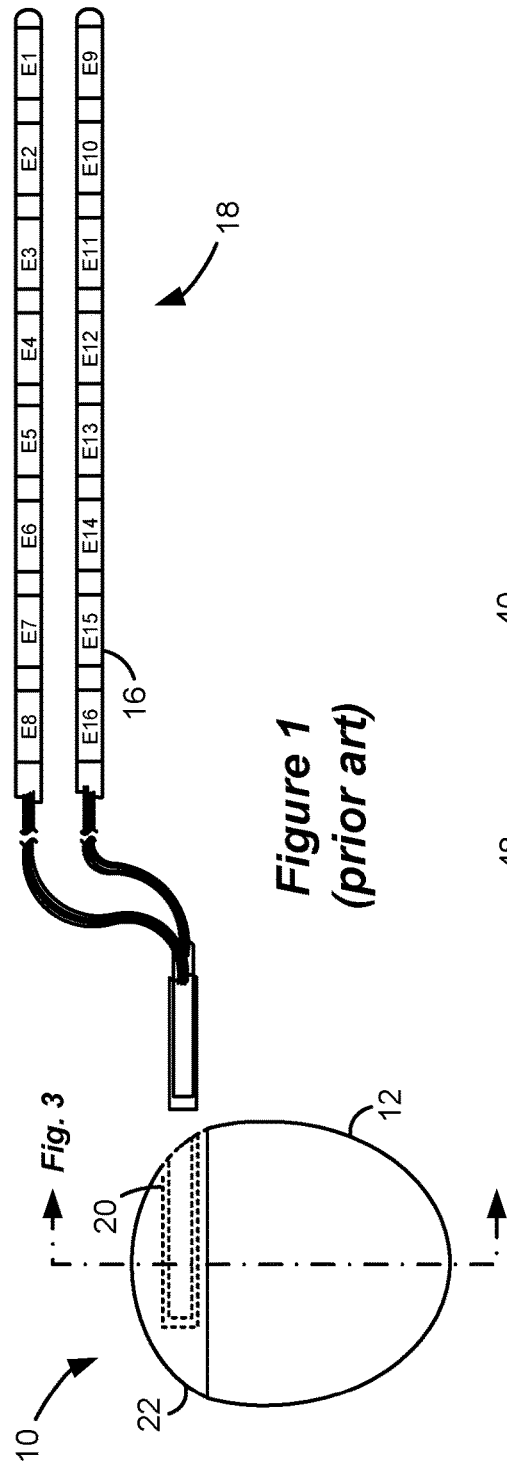
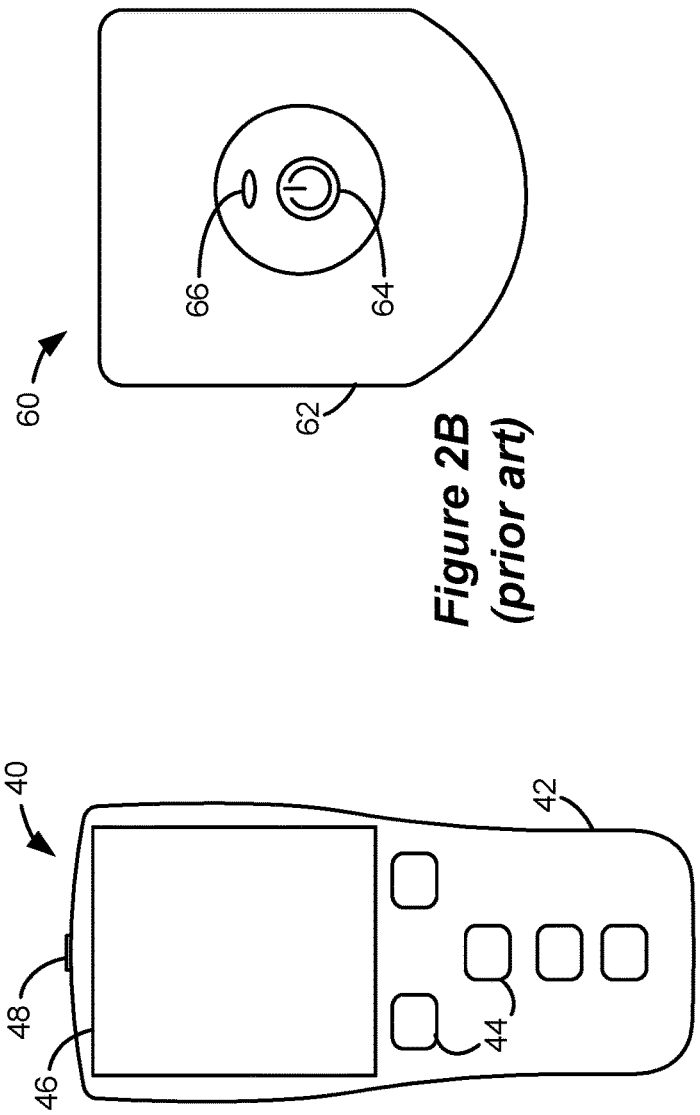
Figure 1 (prior art)
Figure 2A (prior art)
Figure 2B (prior art)

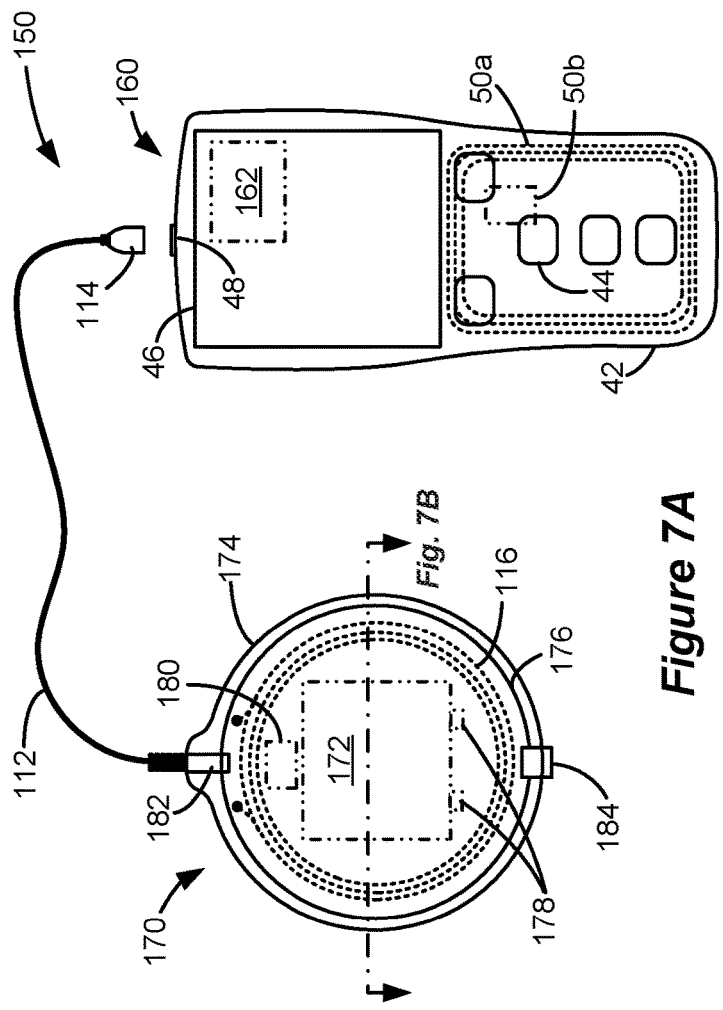
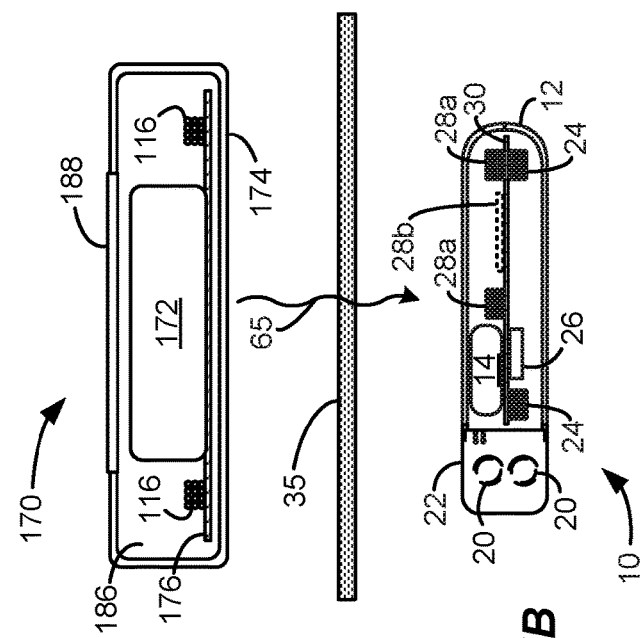
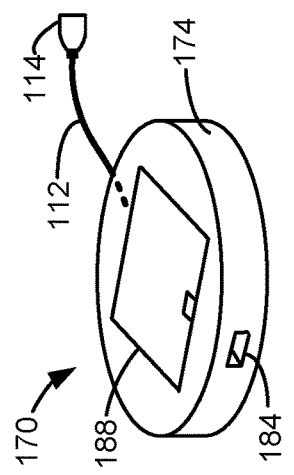
*Figure 7A*
*Figure 7B*
*Figure 7C*

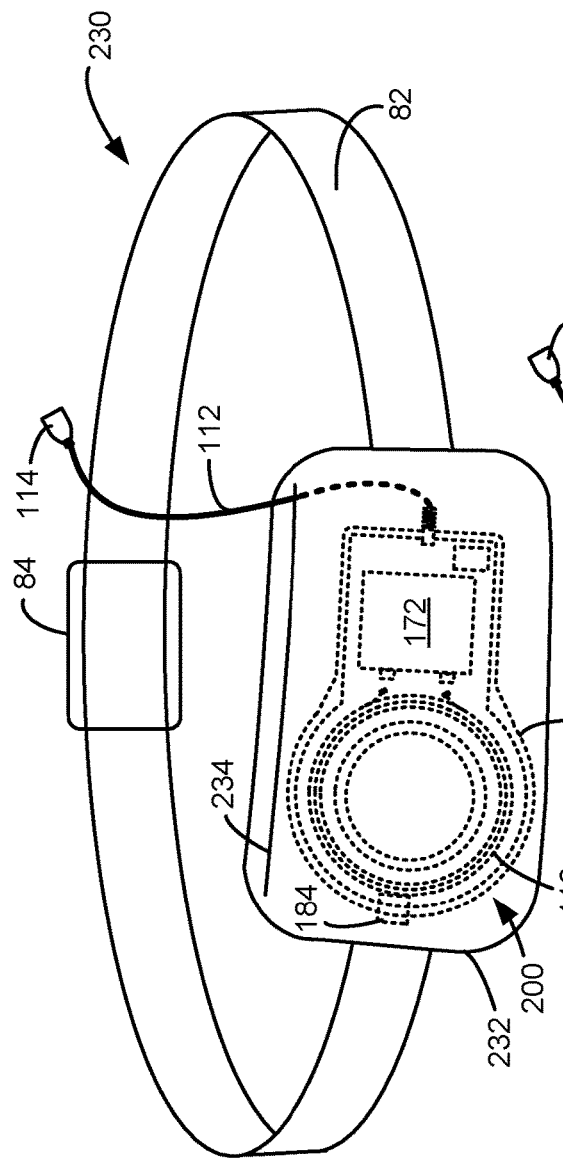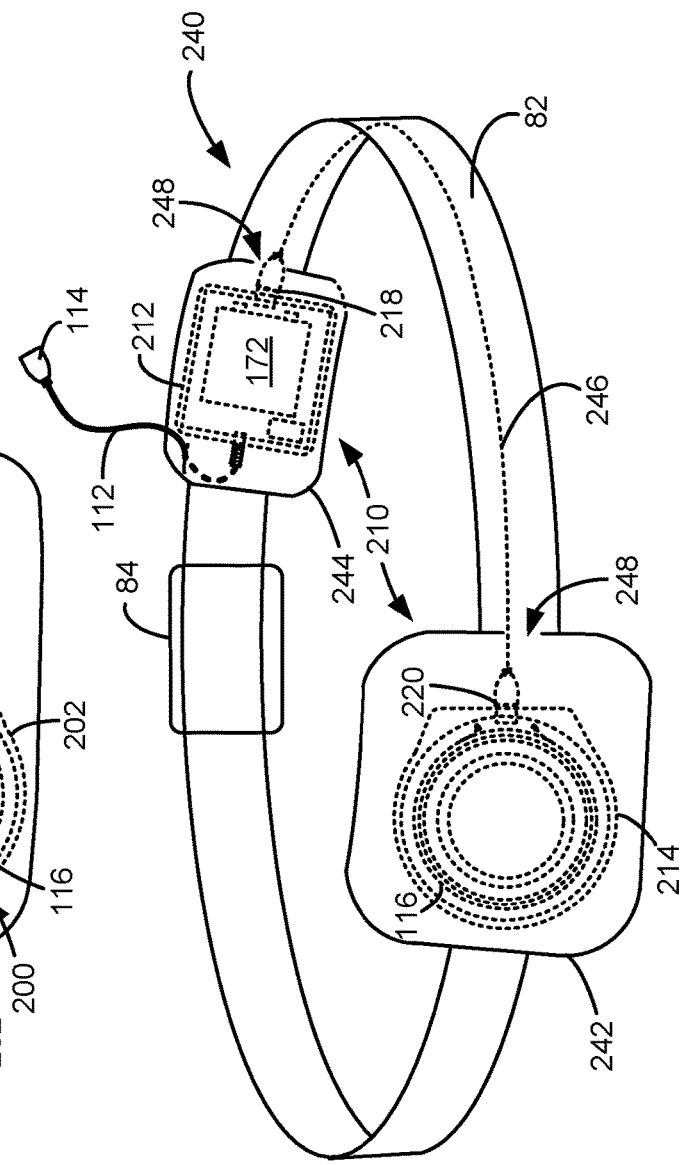

EXTERNAL CONTROLLER FOR AN IMPLANTABLE MEDICAL DEVICE SYSTEM WITH AN EXTERNAL CHARGING COIL POWERED BY AN EXTERNAL BATTERY

CROSS REFERENCE TO RELATED APPLICATIONS

This application is a continuation of U.S. patent application Ser. No. 14/826,050, filed Aug. 13, 2015, which is a non-provisional of U.S. Provisional Patent Application Ser. No. 62/072,737, filed Oct. 30, 2014, which are incorporated by reference in their entireties, and to which priority is claimed.

FIELD OF THE INVENTION

The present invention relates to a data telemetry and power transfer system having particular applicability to implantable medical device systems.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within a spinal cord stimulation (SCS) system, such as that disclosed in U.S. Pat. No. 6,516,227. However, the present invention may find applicability with any implantable medical device (IMD) or in any IMD system.

As shown in FIG. 1, a SCS system includes an Implantable Pulse Generator (IPG) 10 (hereinafter, and more generically, IMD 10), which includes a biocompatible device case 12 formed of titanium for example. The case 12 typically holds the circuitry and battery 14 (FIG. 3) necessary for the IMD 10 to function. The IMD 10 is coupled to electrodes 16 via one or more electrode leads 18 (two of which are shown). The proximal ends of the leads 18 are coupled to the IMD 10 at one or more lead connectors 20 fixed in a header 22, which can comprise an epoxy for example. There are sixteen electrodes (E1-E16) in the illustrated example, although the number of leads and electrodes is application specific and therefore can vary. In an SCS application, two electrode leads 18 are typically implanted on the right and left side of the dura within the patient's spinal column. The proximal ends of the leads 18 are then tunneled through the patient's tissue 35 (FIG. 3) to a distant location, such as the buttocks, where the IMD case 12 is implanted, at which point they are coupled to the lead connectors 20.

An IMD 10 is typically supported by and communicates with one or more external devices, and FIGS. 2A and 2B provide examples of such devices. FIG. 2A depicts an external controller 40 for the IMD 10. The external controller 40 is used to establish a bi-directional wireless data link 45 with the IMD 10, as explained further with respect to FIG. 3. The external controller 40 is typically used to send or adjust the therapy settings the IMD 10 will provide to the patient. If the IMD 10 is an IPG 10 as depicted in FIG. 1, such therapy settings may include which electrodes 16 are active to issue therapeutic current pulses; whether such electrodes sink or source current (i.e., electrode polarity); the duration, frequency, and amplitude of the pulses, etc., which settings together comprise a stimulation program for the IMD 10. External controller 40 can also act as a receiver of data from the IMD 10, such as various data reporting on the IMD's status and the level of the IMD's battery 14.

As shown in FIG. 2A, external controller 40 is typically configured in a hand-held, portable housing 42, and powered by an internal battery (52; FIG. 3), which battery may be a primary battery or rechargeable. The external controller 40 includes a graphical user interface (GUI) similar to that used for a cell phone, including buttons 44 and a screen 46, and may have other interface aspects as well, such as a speaker. While an external controller 40 is typically a device custom built by the manufacturer of the IMD 10 and dedicated in its functionality to IMD communications, external controller 40 may also comprise general purpose, freely programmable mobile device having suitable wireless communication functionality, such as a smart cell phone. In this case, a Medical Device Application (MDA) can be executed on the mobile device to configure it for use as an IMD external controller, and to allow for control and monitoring of the IMD 10. See, e.g., U.S. Pat. No. 9,186,518, which is incorporated herein by reference in its entirety.

FIG. 2B depicts an external charger 60 for the IMD 10, which is used to recharge the IMD 10's rechargeable battery 14 by producing an AC magnetic charging field 65 (FIG. 3). The user interface of the external charger may be simple compared to the external controller 40. For example, the external charger 60 may lack a screen. Instead, the external charger 60 may simply include an on/off button 62 for magnetic charging field 65 generation, and status light emitting diode (LED) 64. Although not shown, external charger 60 may also include a speaker useful to indicate alignment between the external charger and the IMD 10, as is well known. See, e.g., U.S. Patent Application Publication 2013/0096651. External charger 60 is also typically hand-held and portable, and integrated within a housing 62.

Internal structures of the external controller 40, the external charger 60, and the IMD 10 are shown in cross section in FIG. 3, which also depicts the bi-directional data link 45 between the external controller 40 and the IMD 10, and the magnetic charging field 65 produced by the external controller 60.

IMD 10 as shown in FIG. 3 includes the battery 14 mentioned earlier. Although an IMD 10 can include a primary (non-rechargeable) battery, battery 14 in this example is rechargeable. Recharging of the battery 14 is assisted by a charging coil 24. The magnetic charging field 65 from the external charger 60 induces a current in this charging coil 24, which current is then rectified to DC levels and used to charge the battery 14.

The magnetic charging field 65 is produced by a charging coil 66 in the external charger 60. Power for the production of the magnetic charging field 65 is provided by a battery 68 in the external charger 60, which may be primary or rechargeable. The coil 66 is typically electrically coupled to one or more circuit boards 70, 72 in the external charger 60, as is other circuitry 74 (control circuitry such as a microcontroller; coil driver circuitry, etc.). In the configuration shown in FIG. 3, circuitry 74 is affixed to a vertical circuit board 72 to reduce the generation in the circuitry 74 of Eddy currents caused by the magnetic charging field 65. Such Eddy currents may generate heat unwanted heat, providing a patient safety risk, and will also generally detract from the efficiency of power transfer by sinking some of the energy in the magnetic charging field 65. The battery 68 is also moved outside of the charging coil 66 for the same reason, as its typically-metallic case can also heat and sink magnetic charging field 65 energy. Magnetic charging field 65 may comprises a field of 80 kHz for example, and may not be modulated with data. However, Load Shift Keying (LSK) may be used to transmit data back to the external charger 60 during production of the magnetic charging field 65, as is well known. See, e.g., the '651 Publication.

Because charging the battery 14 in the IMD 10 may take some time, it is desired to hold the external charger 60 in close proximity to and in alignment with the IMD 10 during a charging session when the magnetic charging field 65 is produced. Typically, and as disclosed in U.S. Publication 2014/0025140, this occurs using an external charger holding device 80, such as a belt 82, as shown in FIG. 4. The belt 82 fastens around the patient's waist, and can be secured by a fastening device 84, such as a buckle, clasp, snaps, Velcro, etc. The belt 82 can be adjustable to fit patients with different waist sizes. The belt 82 includes a pouch 86, which is generally located on the belt 82 in a position where the IMD 10 is implanted in the patient, such as the back of the patient proximate to the buttocks. A slot 88 or other opening in the belt 82 allows the external charger 60 to be inserted into the pouch 86, such that the external changer 60 is, like the pouch 86, generally aligned with the IMD 10. Once placed in the pouch 86, the patient can press the on/off switch 64 (FIG. 3) on the external charger 60 to begin a charging session—i.e., to produce magnetic charging field 65—or the user can turn the charger on before inserting it in the pouch 86. Affixing the external charger 60 to the patient using belt 82 allows the patient to move or walk while using the external charger 60, and thus can charge his implant "on the go." See also U.S. Publication 2012/0012630, describing another belt for an external charger.

Data communications between the IMD 10 and the external controller 40 (FIG. 2A) along link 45 is assisted by a telemetry antenna 28 in the IMD 10, as shown in FIG. 3. Telemetry antenna 28 can take different forms depending on the physics of the link 45. If magnetic induction is used with link 45 comprising an AC magnetic field, the antenna can comprise a coil antenna 28a. In this case, the antenna 50 provided in the external controller 40 may likewise comprise a coil antenna 50a. If short-range but far-field electromagnetic RF telemetry is used for link 45, the antenna in the IMD 10 can comprise an RF antenna 28b, such as a wire, slot, or patch antenna, as shown in dotted lines. In this case, the telemetry antenna 50 provided in the external controller 40 may likewise comprise an RF antenna 50b, as explained further in the above-incorporated '518 Patent.

Telemetry antenna 28 in the IMD 10 and telemetry antenna 50 in the external controller 40 preferably act to both transmit and receive data. As such, antennas 28 and 50 are respectively coupled to circuitries 26 and 56 to modulate transmitted data and demodulate received data according to a data scheme employed on link 45. For example, if coil antennas 28a and 50a are respectively employed in the IMD 10 and external controller 40, Frequency Shift Keying (FSK) can be used to modulate transmitted data on the link 45. As one skilled in the art understands, this scheme transmits a serial string of data bits, with individual bits being defined by a frequency shift with respect to a nominal center frequency. If the center frequency for data on link 45 comprises 125 kHz for example, a '0' bit may be represented as a transmission at 121 kHz, while a '1' may be represented as a transmission at 129 kHz. Although not shown, one or more orthogonal coil antennas 50a driven or received out of phase could be used in external controller 40 as well to improve communication coupling with the IMD 10 along link 45, as discussed in U.S. Publication 2009/0069869, with which the reader is assumed familiar. If RF antennas 28b and 50b are respectively employed in the IMD 10 and external controller 40, short-range RF schemes may be used on link 45, such as Bluetooth, WiFi, or the Medical Implant Communication Service (MICS), as explained further in the above-incorporated '518 Patent. These are merely examples of telemetry schemes useable on link 45, and other means of communication could be used as well.

One skilled in the art will understand that circuitries 26 and 56 can additionally include other circuits needed for IMD 10 and external controller 40 functionality, and may include control circuits such as a microcontroller. Circuitry 26 in the IMD 10 may additionally include stimulation circuitry for forming the therapeutic current pulses defined by the stimulation program at the electrodes 16 (when IMD 10 comprises an IPG). Electrical components in the IMD 10 and external controller 40 are respectively coupled to circuit boards 30 and 54 as shown.

Transmission of data (link 45) or power (link 65) occurs transcutaneously, i.e., through the patient's tissue 35, which is particularly useful in an implantable medical device system.

Although the external controller 40 and external charger 60 are depicted separately to this point, the art has recognized that the functionality of both of these devices can be integrated into a single device or system. One example disclosed in U.S. Pat. No. 8,335,569 depicts a combined integrated external controller/charger having a single housing, which housing includes the antennas (coils) necessary for both IMD data telemetry and IMD battery charging functions.

Another example of an integrated external controller/charger system 90 is depicted in FIGS. 5A and 5B, as disclosed in U.S. Pat. No. 8,498,716, which is incorporated herein by reference in its entirety. As shown in FIG. 5A, system 90 includes an integrated external controller/charger 100 that can be similar in construction and function to the external controller 40 (FIG. 2A). Thus, the integrated external controller/charger 100 again includes a hand-held, portable housing 42 and a GUI including buttons 44 and a screen 46. Housing 42 may also again contain one or more antennas 50a or 50b for communicating with the IMD 10 via a link 45 (FIG. 3), to transmit therapy settings or to receive IMD status information for example.

However, unlike the external controller 40 of FIG. 2A, the integrated external controller/charger 100 additionally contains circuitry to drive an external charging coil assembly 110, which is attachable via a cable 112 and connector 114 to a port 48 (e.g., a USB port) on the housing 42. The external charging coil assembly 110 includes a charging coil 116 similar in function to the coil 66 used in the external charger 60 (FIGS. 2B, 3). Charging coil 116 may be mounted to a substrate 118 in the assembly 110, which may comprise a circuit board, and may include contact points for ends of the charging coil 116 and for the termination 120 of the signals in cable 112. Substrate 118 may be flexible, such as made of polyimide or Kapton for example, or rigid like a traditional printed circuit board. The external charging coil assembly 100 may include a housing 122 for the coil 116 and substrate 118, which may comprise an overmolded material such as silicone or hard plastic for example. As shown, a hole 124 may be present in the housing 122 of the assembly 110 in the center of the charging coil 116. Although not shown, the external charging coil assembly 110 may additionally contain one or more temperature sensing devices, such as thermistors or thermocouples, to measure the temperature of the assembly 110 and to report such temperature to the external controller/charger 100 so that production of the magnetic charging field 65 can be controlled accordingly (e.g., so as to not exceed a safe temperature set point).

The external controller/charger 100 is additionally programmed to allow a user to charge the IMD battery 14 via the external charging coil assembly 110 using the GUI of the device 100, with appropriate user selection at the GUI causing magnetic charging field 65 to be produced, as shown in FIG. 5B.

The implementation of the integrated external controller/charger system 90 is touted in the '716 Patent as beneficial, as it achieves good integration of the charging and data telemetry. Because the external charging coil assembly 110 does not contain substantial electronics, such as its own display, battery, microcontroller, etc., it is less bulky and easier to carry in conjunction with the external controller/charger 100. Moreover, the external charging coil assembly 110 lacks its own user interface, and instead the GUI of the external controller/charger 100 is used to control and monitor IMD charging functionality. This makes system 90 easy to use, as the patient does not need to learn how to use or manipulate two completely independent devices—i.e., an external controller 40 (FIG. 2A) and an external charger 60 (FIG. 2B). The '716 Patent further notes that because the external controller/charger 100 powers both itself and the external charging coil assembly 110 via the battery 52 internal to its housing 42 (FIG. 3), there is only one battery to replace and/or recharge in the system 90.

SUMMARY OF THE INVENTION

Charging coil assemblies for use with a medical device such as IMD 10 are disclosed. The assembly in one example comprises a first connector configured to couple to a first port of an external controller; a charging coil configured to produce a magnetic charging field for the medical device under control of the external controller via the first connector; and a battery configured to power the first circuitry to energize the charging coil to produce the magnetic charging field. The charging coil assemblies may not contain a user interface, although the external controller may include a user interface to both monitor and control the medical device, and to control charging of the medical device.

The charging coil assemblies may include a housing, within which the charging coil and the battery are placed. The battery may be within an area defined by the charging coil, or outside of that area. The disclosed assemblies may include a holding device configured to be wearable by a medical device patient to hold the housing proximate to the medical device of the patient.

The charging coil assemblies may also include a first housing containing the charging coil and a second housing containing the battery, which housings are electrically coupled. In this example, the wearable holding device may locate the first and second housings at different positions on the holding device.

The first circuitry for energizing the charging coil, such as an amplifier, may be within the external controller, with the first connector including a first signal to send a first voltage provided or generated from the battery to the first circuitry, and second signals coupled to ends of the charging coil. The first voltage may be coupled to a pin on the first connector corresponding with a pin of the first port meeting with battery recharging circuitry in the external controller. The amplifier may alternatively place the first voltage and its inverse across the charging coil, and/or the amplifier may place the first voltage across the charging coil at or substantially near a resonant frequency of the charging coil.

The charging coil assemblies may include battery covers in their housings to permit a user access to the battery, and may include a second port and battery recharging circuitry, with second port receiving a second connector to recharge the battery. The assembly may also include at least one temperature sensor, with a temperature determined by the at least one temperature sensor being reported to the external controller via the first connector. The first connector of the assembly is preferably attachable to and detachable from the first port of the external controller. The battery of the charging coil assemblies may only power the first circuitry used to energize the coil, and may not power other circuitry in the external controller.

The charging coil assemblies may include communication interface circuitry coupled to the first connector, which circuitry controls communications with the first port of the external controller as a master. The communication interface circuitry may receive at least one indication from the first port of the external controller to cause the first circuitry to be powered to energize the charging coil to produce the magnetic charging field.

A system for use with a medical device is also disclosed including an external controller, which may comprise a mobile device such as a cell phone or an optical head mounted display, and a charging coil assembly, such as those just described. The external controller can include at least one antenna for communicating data with the medical device, and a first battery separate from the battery of the charging coil assembly. The at least one antenna comprises at least one coil antenna for communicating data via magnetic inductive coupling, or can communicate data via short-range electromagnetic RF telemetry. Such data communication may be used to monitor and/or control the medical device.

Another system for use with a medical device can include a non-transitory machine-readable medium upon which are stored instructions for a medical device application executable by a mobile device. When the medical device application is executed on the mobile device, the medical device application will provide a Graphical User Interface (GUI) on the mobile device to allow a user to communicate data between the mobile device and a medical device, and to control charging of the medical device. Such charging control can be accomplished using the charging coil assemblies described, which again can include a first connector for coupling to a first port of a mobile device executing the medical device application.

BRIEF DESCRIPTION OF THE DRAWINGS

FIG. 1 shows an implantable pulse generator (IPG) type of implantable medical device (IMD), and the manner in which an electrode array is coupled to the IPG, in accordance with the prior art.

FIGS. 2A and 2B show external devices for an IMD, specifically an external controller (FIG. 2A) and an external charger (FIG. 2B), in accordance with the prior art.

FIG. 7A shows an improved integrated external controller/charger system comprising an improved external controller/charger device with a smaller capacity battery and an improved detachable external charging coil assembly with a larger capacity battery; FIG. 7B shows the improved assembly in communication with the IMD; and FIG. 7C shows a perspective view of the improved assembly, in accordance with an example of the invention.

FIGS. 10A and 10B show holding devices such as belts useable with the improved external charging coil assemblies, in accordance with examples of the invention.

DETAILED DESCRIPTION

Figure 3:
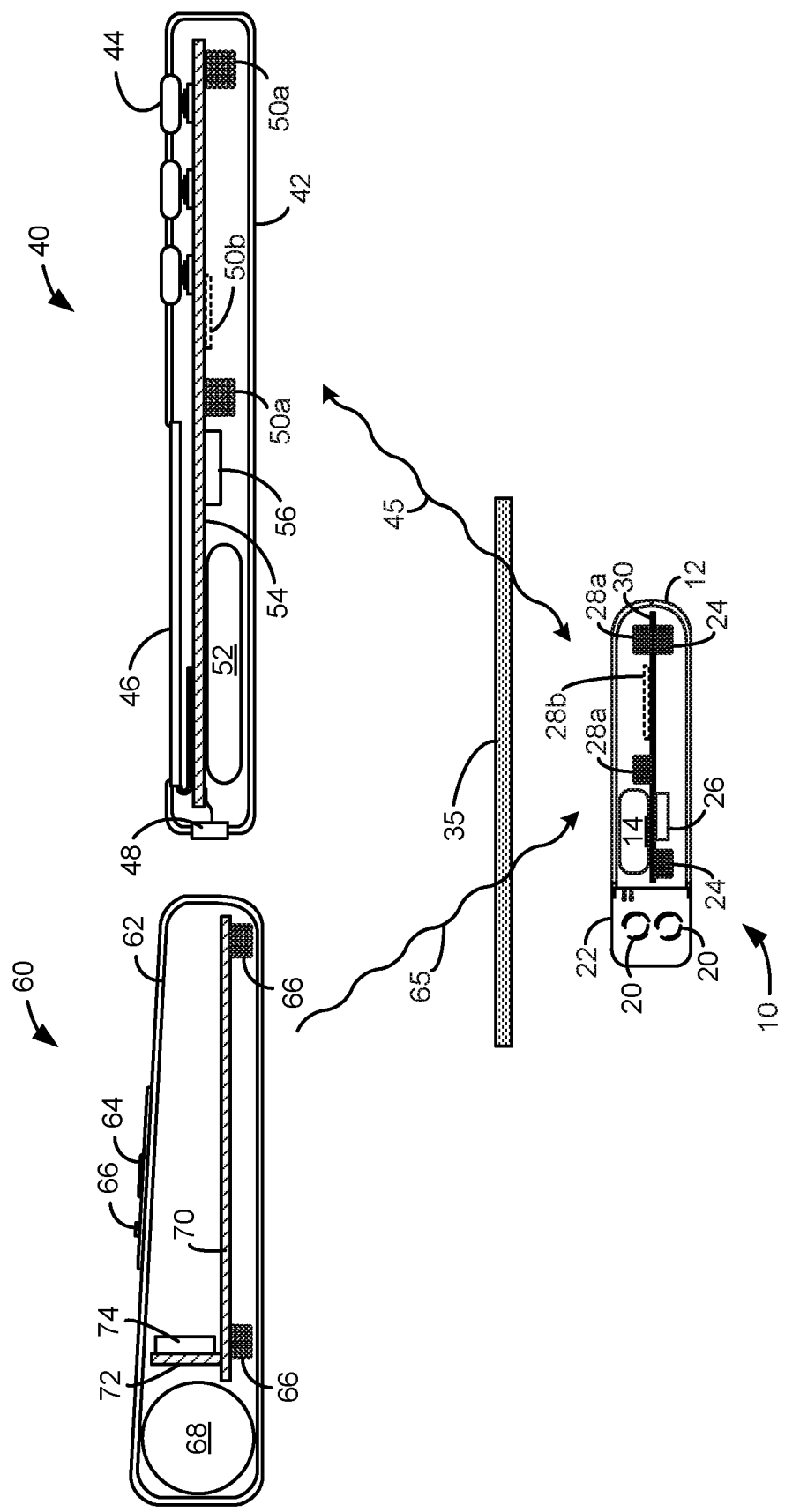
FIG. 3 shows the IMD, the external controller, and the external charger in cross section, and shows wireless communication of data between the external controller and the IMD, and wireless transfer of power from the external charger to the IMD, in accordance with the prior art.
Figure 5A:
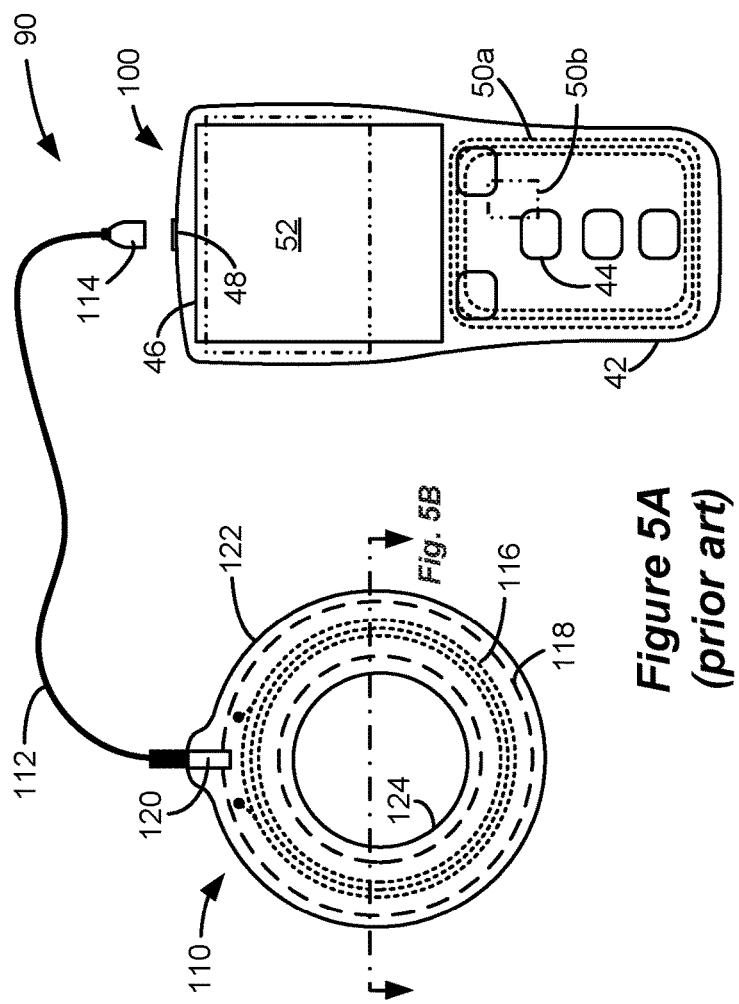
FIG. 5A shows an integrated external controller/charger system comprising an external controller/charger device with a detachable external charging coil assembly.
Figure 5B:
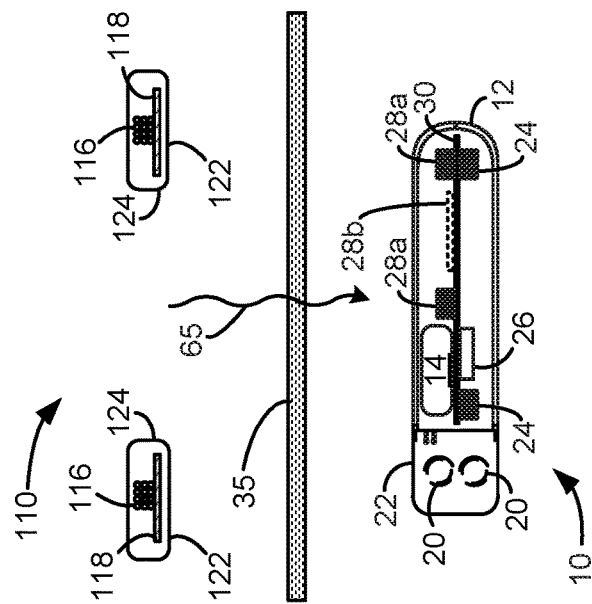
FIG. 5B shows the assembly in communication with the IMD, in accordance with the prior art.
Figure 6:
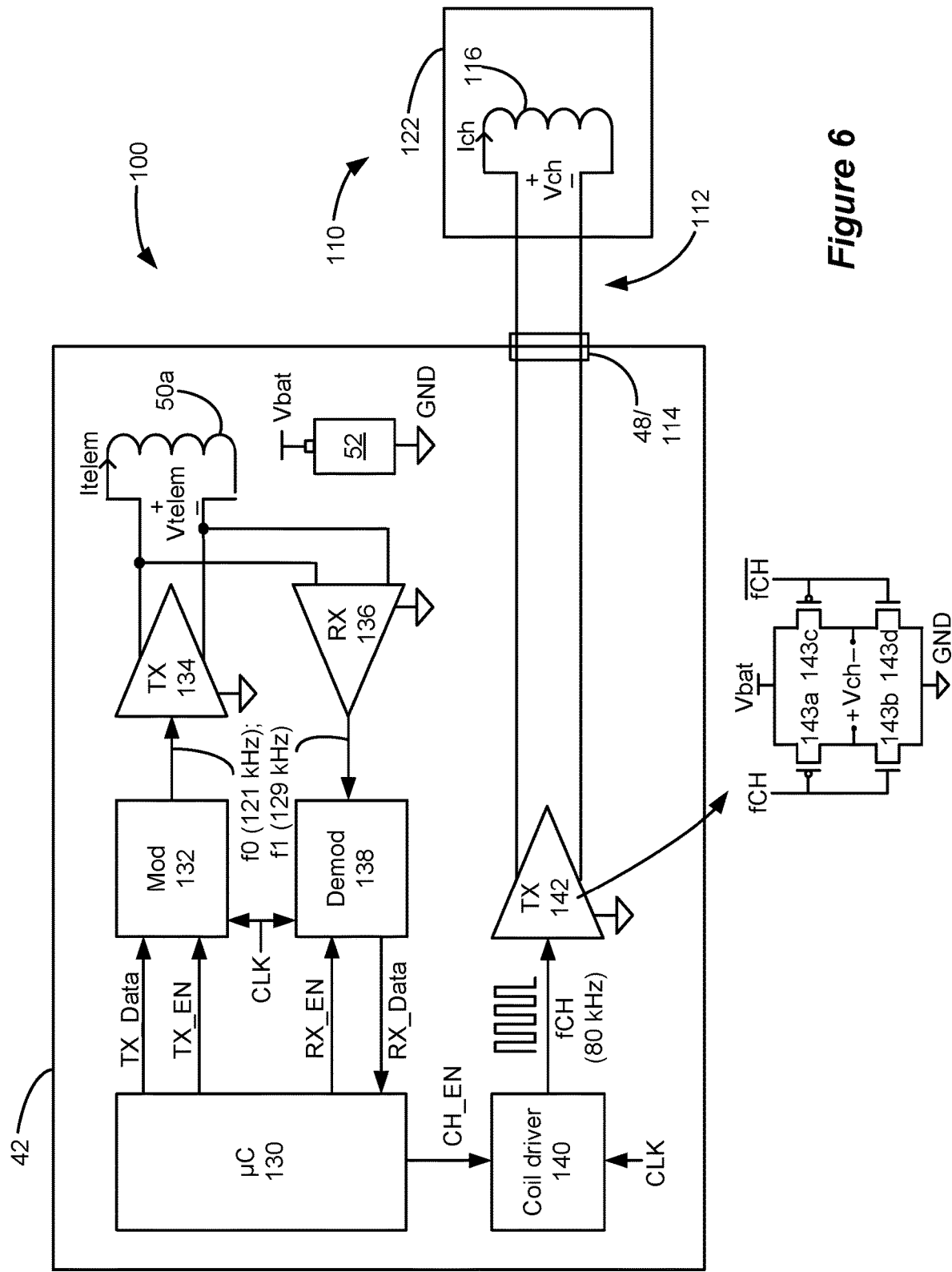
FIG. 6 shows an example of circuitry present in the external controller/charger system device and the external charging coil assembly of FIG. 5A.

The inventors see value in the integrated external controller/charger system 90 as disclosed in U.S. Pat. No. 8,498,716 and as depicted here in FIGS. 5A and 5B. However, the inventors also see shortcomings with this approach, particularly as concern system power. Although the '716 Patent doesn't disclose the internal circuitry of its integrated external controller/charger 100, the inventors would configure such circuitry as shown here in FIG. 6. In FIG. 6, the external controller/charger 100 is depicted as having a magnetic induction coil antenna 50a for telemetry with the IMD 10 as taught in the '716 Patent, although the inventors recognize that an RF antenna 50b (FIG. 3) could also be used depending on the antenna 28 used in the IMD 10 and the particulars of wireless data link 45.

As shown, the external controller/charger 100 includes control circuitry, such as a microcontroller 130. The microcontroller 130 can control the reception (RX) of data from the IMD 10 (e.g., status information) at coil antenna 50a inside the device housing 42; the transmission (TX) of data from the coil antenna 50a to the IMD 10 (e.g., therapy settings or adjustments); and the production of the magnetic charging field 65 (CH) from charging coil 116 in the housing 122 of the external charging coil assembly 110. Each of these functionalities can be enabled by the microcontroller 130 via enable signals TX_EN, RX_EN, and CH_EN respectively. While data reception (RX_EN) and transmission (TX_EN) would preferably not be enabled at the same time, charging (CH_EN) could be simultaneously enabled with either. CH_EN may be asserted by the microcontroller 130 when the patient selects charging options on the GUI of the external controller/charger 100.

A string of digital data bits to be transmitted (TX_Data) are provided to a modulator 132, which will encode the data in accordance with the telemetry scheme to be used along link 45 (e.g., FSK, Bluetooth, etc.). Modulator 132 would preferably also receive an AC signal (CLK) to so encode the data, the frequency of which preferably matches the nominal frequency of the data to be transmitted on link 45. For example, CLK might comprise a 125 kHz signal in an FSK communication scheme, with modulator 132 shifting that frequency in accordance with the digital data state (either '0' or '1') of particular data bits in TX_data (either f0=121 kHz or f1=129 kHz). AC signal CLK may be provided or derived from a crystal oscillator or another type of oscillator circuit (e.g., a ring oscillator, a phase locked loop, etc.).

The modulated data to be transmitted is then sent to a data transmitting amplifier TX 134 to provide a suitably strong signal to the coil antenna 50a. The transmitting amplifier TX 134 as controlled by the modulated data will cause an AC voltage (Vtelem) to be produced across the coil antenna 50a, causing an AC current (Itelem) to flow through the coil antenna 50a in accordance with its impedance. One skilled will understand that coil antenna 50a preferably comprises a resonant LC tank circuit, with inductance L being provided by the coil antenna 50a, and C being provided by a capacitor (not shown) either in series or parallel with the coil antenna 50a. This tank circuit should have a natural resonant frequency close to that of the modulated data—e.g., the center frequency of 125 kHz.

Although less relevant here, data reception from the IMD 10 occurs using the same coil antenna 50a. A voltage differential (Vtelem) as induced by the magnetic field of link 45 carrying data transmitted from the IMD 10 is provided to a data receiving amplifier RX 136 to amplify this difference. The amplified modulated data is then provided to a demodulator 138 to decode the modulated data into a string of digital data bits (RX_Data) for interpretation by the microcontroller 130. As one skilled in the art will understand, the demodulator 138 is assisted in its decoding task by receipt of an AC signal, which may be the same as received by the modulator 132 (CLK) or different.

Transmission of power to the IMD 10 from charging coil 116 in the external charging coil assembly 110 starts with the assertion of charging enable signal, CH_EN. As shown, this signal is met by coil driver circuitry 140 to generate an AC signal (fCH) matching the frequency of the magnetic charging field 65 to be produced (e.g., 80 kHz), and at or substantially near (e.g., +/−10%) the resonant frequency of the resonant LC tank circuit comprising charging coil 116. Again, the capacitor for this tank circuit is not shown, but presumably could be within the housing 42 of the external controller charger 100, or within the housing 122 of the external charging coil assembly 110.

As alluded to earlier, fCH may not be modulated with data, and hence may comprise a signal of constant amplitude and frequency. fCH is presented to a charging transmitting amplifier TX 142, which will cause an AC voltage (Vch) to be produced across the charging coil 116, causing an AC current (Ich) to flow through the coil antenna 50a in accordance with its impedance. In the non-limiting example shown at the bottom of FIG. 6, the charging transmitting amplifier 142 comprises transistors 143a-d which when controlled by fCH and its complement alternatively place the voltage of battery 52 (Vbat; 143a and d open; 143b and c closed) and its inverse (-Vbat; 143a and d closed; 143b and c open) across the charging coil 116. However, this is strictly one example of charging transmitting amplifier, and other amplifier circuits may be used, including those that only place a single polarity of Vbat across the coil 116 and those that are controlled with only a single (non-complementary) input. For example, a well-known Class E amplifier could be used as well. The charging transmitting amplifier 142 is coupled to the charging coil 116 via the port 48 on the device housing 42, and via connecter 114 and cable 112 of the external charging coil assembly 110.

Note that the '716 Patent stresses that the power for all circuitry in FIG. 6 is provided by the external controller/charger's battery 52 (Vbat). The inventors recognize that microcontroller 130, modulator 132, receiver 136, demodulator 138, coil driver 140, and other circuitry in system 90 use relatively small amounts of battery 52 power.

By contrast, the inventors recognize that the data transmitting amplifier 134 and the charging transmitting amplifier 142 use significantly more power than the circuits just mentioned as they are respectively responsible for energizing data coil antenna 50a and charging coil 116 to create magnetic fields (data link 45 and magnetic charging field 65) of a sufficient strength to be received with useful effect at the IMD 10—i.e., at IMD coil antenna 28a and IMD charging coil 24 respectively. Generally speaking, these amplifiers 143 and 142 will draw power at least equal to their output powers. In other words, data transmitting amplifier 134 will draw at least Vtelem*Itelem, and the charging transmitting amplifier 142 will draw at least Vch*Ich, from the battery 52 in the external controller/charger 100.

Of these two transmitting amplifiers 134 and 142, the inventors notice that the latter (142) requires much more power than the former (134). There are several reasons for this. First, data transmission on link 45 needs only to be of a power sufficient to produce in the IMD's telemetry coil antenna 28a a relatively small signal (on the order of tenths of Volts and a few milliamps) that the IMD 10's receiver circuitry (not shown) can reliably resolve. By contrast, the magnetic charging field 65 must be of a power sufficient to produce much bigger signals at the IMD's charging coil 24 (on the order of Volts and tens of milliamps) to create a meaningful charging current for the IMD's battery 14. As a result, the magnetic charging field 65 is generally of a much higher power that the field generated to transmit data on link 45. Stated differently, Itelem*Vtelem at data coil antenna 50a is much smaller than Vch*Ich at the charging coil 116 in the external charging coil assembly 110, by at least an order of magnitude.

Further exacerbating the differences between power requirements for data transmission and power transmission in the integrated external controller/charger system 90 are differences in the times needed for both. The coil antenna 50a in the housing 42 may only need to transmit small amounts of data to the IMD 10, such as updated IMD therapy setting or a new stimulation program, but even a relatively long data communication session will typically occur over a few seconds. By contrast, production of the magnetic charging field 65 from the charging coil 116 during a charging session may take much longer—on the order of minutes or even up to an hour until the IMD battery 14 is fully recharged. Disparity between the power requirements of data transmission and power transmission are even further exacerbated if RF means for telemetry are used on link 45—i.e., if RF antennas 50b and 28b are used in the external controller/charger 100 and the IMD 10—as such RF means of communication generally can occur at lower powers than do magnetic induction means of communication between coil antennas 50a and 28a.

In short, the inventors notice that power requirements in the integrated external controller/charger system 90 are dominated by its charging functionality—i.e., by the production of the magnetic charging field 65 at coil 116 in the external charging coil assembly 110. This means that the battery 52 inside of the external/controller housing 42 must have a large enough capacity to provide the power needed during charging, which generally means that the battery 52 must be relatively large in size. This is unfortunate, as it means that the external controller/charger 100 (i.e., its housing 42) must also be large in size. While a patient may only require charging of his IMD battery 14 every few days or so, and thus will only need to use the external charging coil assembly 110 at those times, the patient will likely always need access to the controller functionality of the external controller/charger 100 to communicate data with his IMD 10. This is true because a patient typically adjusts his IMD therapy settings to different levels throughout the day, and because a patient may need to control his IMD 10 in case of an emergency—for example, if the IMD 10 seems to be malfunctioning and should be turned off. In short, a patient may be advised to always carry his external controller/charger 100 for immediate IMD 10 control. By contrast, and particularly if patient's IMD 10's battery 14 is well charged, a patient may not need to likewise always carry his external charging coil assembly 110.

Even if a patient is inclined to always carry an external charging coil assembly 110 in addition to his external controller/charger 100, the external controller/charger 100 may not always be capable of providing charging functionality that an external charging coil assembly 110 may require. As discussed above and as disclosed in the above-incorporated '518 Patent, other general purpose mobile devices having programmable GUIs and wireless communication functionality, such as smart cell phones, can be used as external controllers for an IMD 10—that is, to communicate data bi-directionally with an IMD 10. However, such mobile devices typically include a battery optimized in size and capacity by the mobile device manufacturer to power the functionality the mobile device is expected to provide—e.g., cell communications, short-range communications (e.g., Bluetooth of WiFi), GUI powering (including the screen), etc.

Use of batteries inherent in such mobile devices to provide a magnetic charging field 65 is not contemplated by mobile device manufacturers, and therefore such inherent batteries may not have a capacity sufficient for the powers (Vch*Ich) required. Making matters worse, the batteries inherent in such mobile devices are generally not modifiable to accommodate the power required for such wireless charging: mobile device manufacturers may prevent user access to the, or at best may allow a user access to merely swap a defective battery for another of like size and capacity. In short, it is difficult at best to provide a battery in a general purpose mobile device sufficient for the high-power task of wirelessly charging an IMD battery 14 via production of a magnetic charging field 65. Simply said, this is because wirelessly charging functionality is not the purpose for which general purpose mobile devices are typically designed, and as such batteries inherent in such mobile devices may not have sufficient capacity to enable such functionality.

Figure 8A:
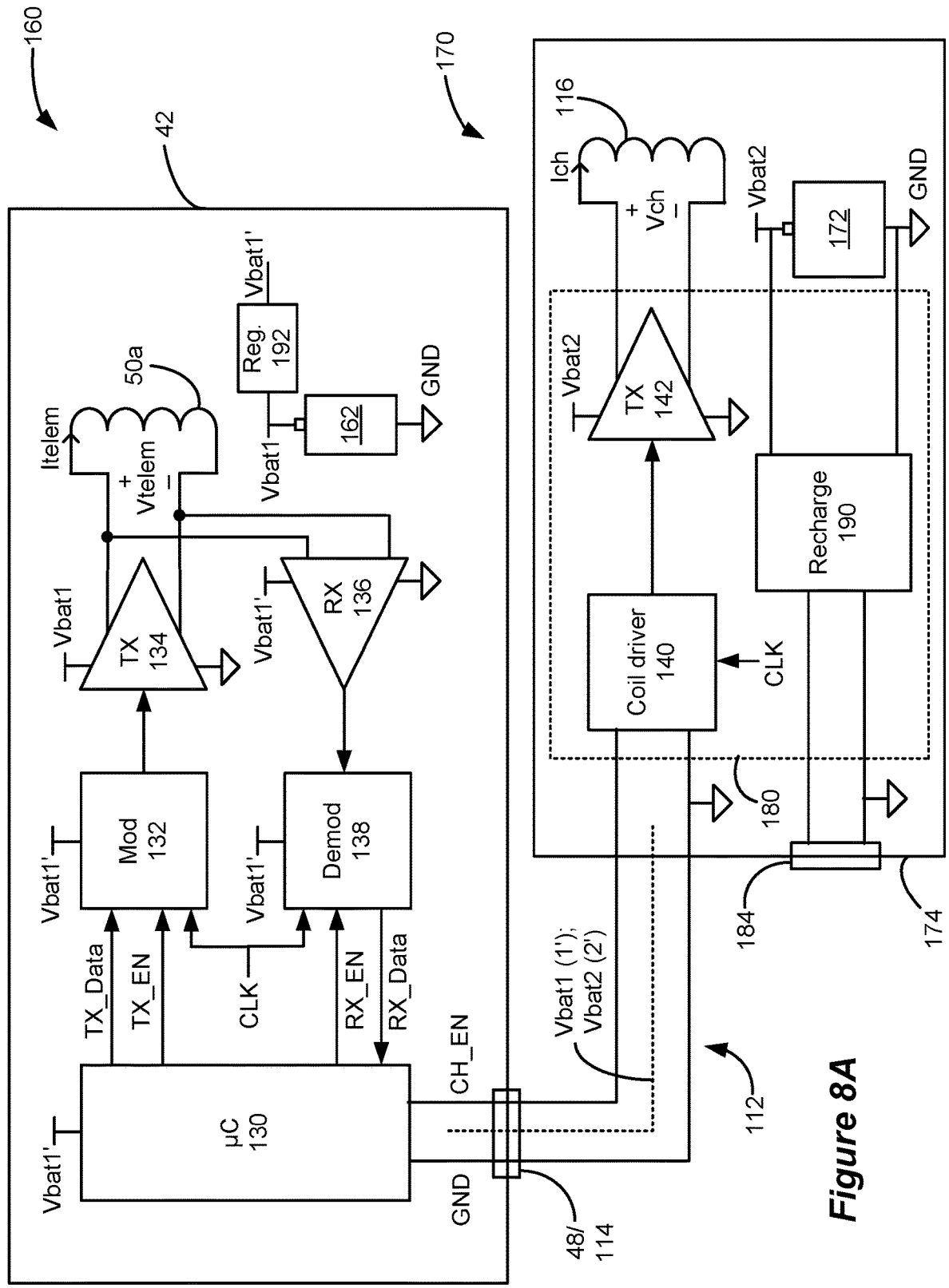
FIGS. 8A-8C show circuitry present in the improved external controller/charger device and the improved external charging coil assembly of FIGS. 7A-7C, in accordance with examples of the invention.
Figure 8B:
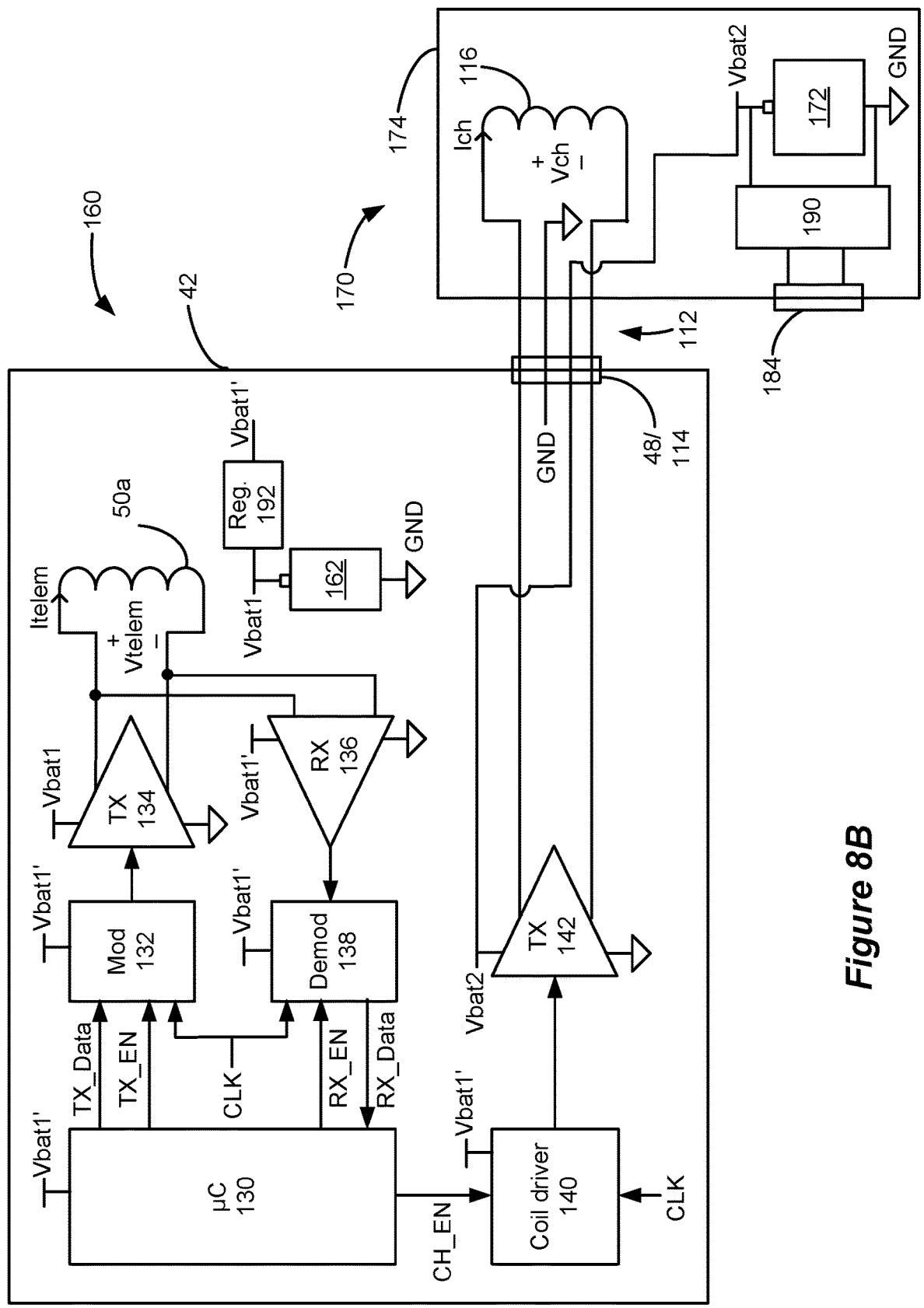
Figure 8C:
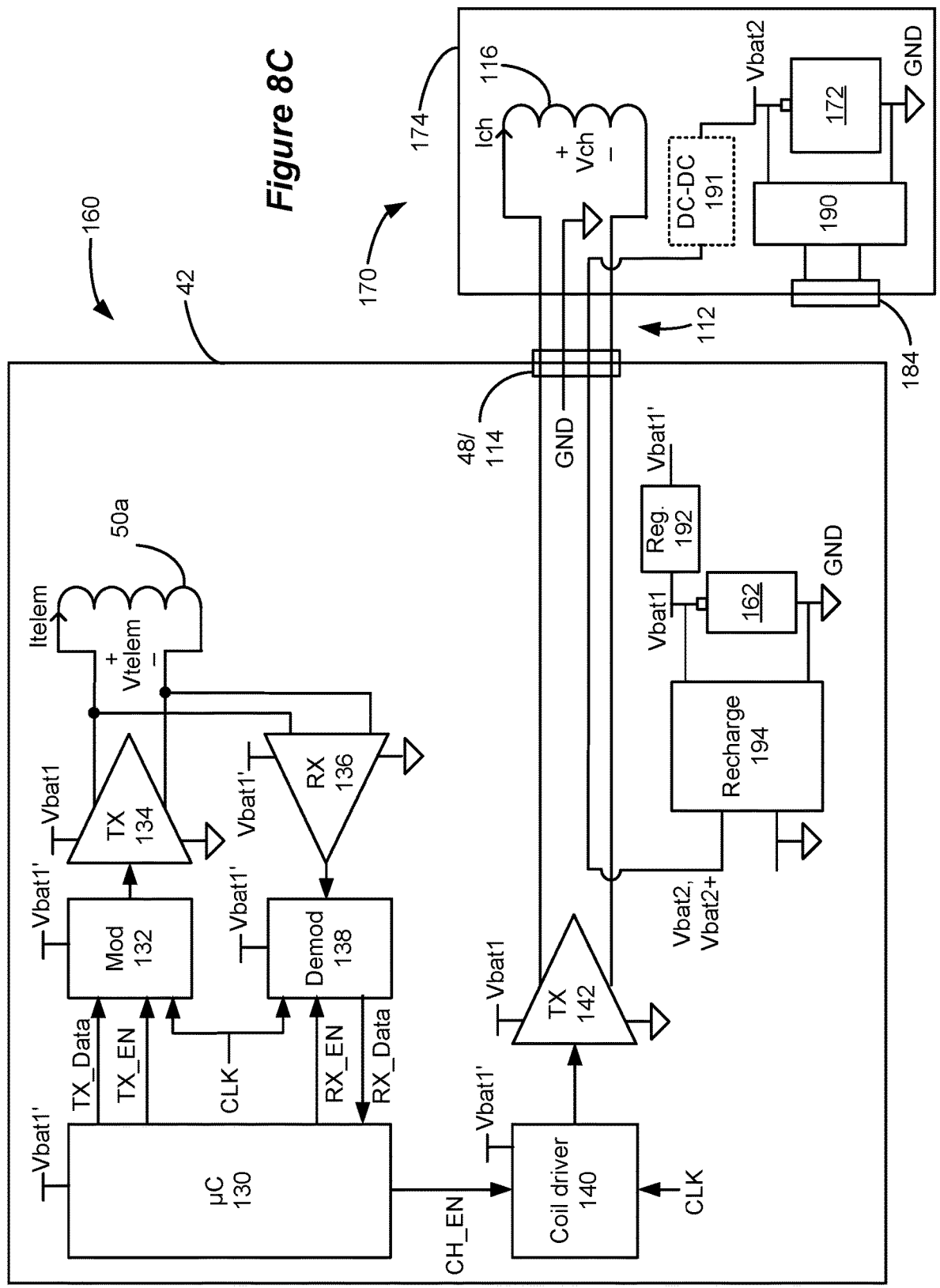

Accordingly, the inventors disclose an improved integrated external controller/charger system 150, whose construction is shown in one example in FIGS. 7A-7C, and whose circuitry is shown in different examples in FIGS. 8A-8C. Many of the components in system 150 can remain unchanged from the system 90 of FIGS. 5A, 5B, and 6, and thus retain the same elements numerals which are not again explained. New to the system 150 is an external controller charger 160 having a much smaller capacity battery 162 (compare battery 52, FIG. 5A), and an external charging coil assembly 170 having an additional larger capacity battery 172. As will be explained further with reference to FIGS. 8A-8C, battery 172 is preferably used to power at least the charging transmitting amplifier 142 used to energize the charging coil 116 in the external charging coil assembly 170, while battery 162 powers other aspects of the system 150, such as data telemetry circuitry and other electronics. Whereas battery 52 in the external controller/charger 100 of FIG. 5A may have a capacity of 1200 mAhr (milliamp hours) for example, battery 162 in the external controller/charger 160 can have a capacity of 800 mAhr, and battery 172 in the external charging coil assembly 170 can have a capacity of 1800 mAhr, in just one non-limiting example.

The additional battery 172 in system 150 can be included in or associated with the external charging coil assembly 170 in a number of different ways. For example, the assembly 170 may lack a hole (compare 124, FIG. 5A) in the assembly housing 174 in the center of the charging coil 116, with this space instead being used to accommodate the battery 172. Thus, and as best shown in FIG. 7B, a substrate 176 in the housing 174 of the external charging coil assembly 170 can be continuous throughout the housing and used to support the battery 174 in addition to the charging coil 116. Additionally, the substrate 176 preferably comprises a circuit board, thus allowing battery 172's terminals 178 to be electrically coupled (e.g., soldered) thereto, along with assembly circuitry 180 to be explained further with reference to FIG. 8A. Wires within cable 112 may also terminate 182 at the circuit board 176, as may ends of the charging coil 116, to allow for proper routing and connection of the electronics in the assembly 170. Although not shown, the battery 172, assembly circuitry 180, and the charging coil 116 could appear on different sides of the substrate 176. Also not shown, the external charging coil assembly 170 may include one or more temperature sensors, as described earlier.

The housing 174 of the external charging coil assembly 170 may comprise overmolded materials. This may prevent access to the battery 172, and hence the ability to change the battery 172 in the assembly 170 if it is primary. Alternatively, battery 172 may be rechargeable, with electrical access to recharge the battery 172 provided by a port 184 (e.g., a USB port) in the assembly housing 174. Although the battery recharging port 184 is shown on the side of the housing 174 in the figures, this is not strictly necessary. Assembly housing 174 may also include an internal cavity 186 for its electronics, and include a battery cover 188 to permit access to the battery 172 to allow it to be changed. Although battery 172 is shown as a singular structure, it should be understood that battery 172 can comprise more than one battery connected in series or parallel as the electronics in the external charging coil assembly 170 dictates. For example, battery 172 may comprise one or more commercial primary batteries, such as a 9-Volt battery, AA or AAA batteries, etc.

Figure 9B:
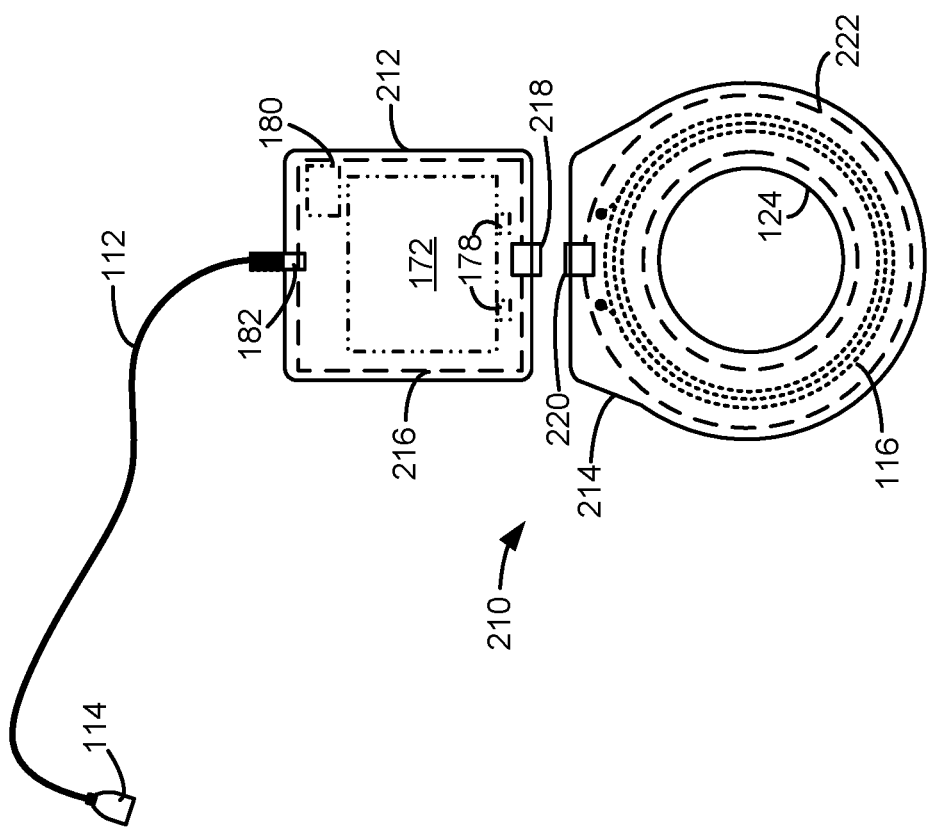
FIGS. 9A and 9B show alternative constructions for the improved external charging coil assemblies incorporating external batteries, in accordance with examples of the invention.

Like the external charging coil assembly 110 explained earlier (FIG. 5A), external charging coil assembly 170 preferably lacks its own user interface, and instead the GUI of the external controller/charger 160 is used to control and monitor IMD charging functionality, as well as to control and monitor IMD operation via antenna 50*a/b*. Alternatively, external charging coil assembly 170 may have a minimal user interface. For example, an indicator, such as one or more LEDs, may be provided on the housing 174 (or on either of housings 212 and 214; FIG. 9B) to indicate the status of the battery 172 (e.g., that it is low; that it is being charged, etc.) Such an indication would preferably be visible through any holding device used (see 230 and 240; FIGS. 10A and 10B). In any event, it may still be preferred that any user interface used for the external charging coil assembly 170 be used merely for indication, and thus may not receive an input from the user.

As shown in the circuit diagram of FIG. 8A and as explained earlier, the housing 42 of the external controller/charger 160 includes the (smaller capacity) battery 162 (providing power supply voltage Vbat1), while the housing 174 of the external charging coil assembly 170 includes the (larger capacity) battery 172 (providing power supply voltage Vbat2). In addition to battery 172, the assembly 170 may also contain assembly circuitry 180, which in the example shown includes certain circuitry moved from the external controller/charger 100 (FIG. 6), such as the coil driver 140 and the charging transmitting amplifier 142. Assembly circuitry 180 may also contain additional circuitry, such as recharging circuitry 190 for interfacing between an external source of power at port 184 and the battery 172 (if it is rechargeable). This modifies the signaling of the wires present in cable 112 of the external charging coil assembly 170. Whereas the wires in cable 112 of assembly 110 (FIG. 6) comprised the ends of the charging coil 116, cable 112 of assembly 170 includes the charge enable signal (CH_EN), which as before is issued to the coil driver 140 in the assembly 1. Also preferably present in cable 92 is a ground signal (GND) to which all circuitry in the external controller/charger 160 and external charging coil assembly 170 can be tied, including the batteries 162 and 172, to ensure a common reference in the system 150.

In a preferred example, all circuitry within the housing 42 of the external controller/charger 160 (microcontroller 130, modulator 132, data transmitting amplifier 134, demodulator 138, data receiving amplifier 136, etc.) is ultimately powered by battery 162 (Vbat1). Such circuitry may receive power from the battery 162 indirectly via a regulator 192 for producing a smaller power supply voltage of a predictable and stable value (Vbat1'). In the example shown, the higher-powered data transmitting amplifier 134 may be powered by Vbat1 directly, while lower-power or digital circuits (microcontroller 130, modulator 132, demodulator 138, data receiving amplifier 136) are powered by regulated supply Vbat1' (although still ultimately powered by Vbat1/battery 162).

Likewise, the assembly circuitry 180 within the housing 174 of the external charging coil assembly 170 (coil driver 140, charging transmitting amplifier 142, recharging circuitry 190 for the battery 172, etc.) is preferably ultimately powered by battery 172 (Vbat2). Although not shown, Vbat2 may also be regulated by a regulator (to Vbat2'), and again, lower-powered or digital circuits (coil driver 140, recharging circuitry 190) may be powered by such regulated power supply voltage, with charging transmitting amplifier 112 powered by Vbat2 directly.

Other signals may be provided in cable 112. For example, and as illustrated via a dotted line, cable 112 may include at least one wire to route power from one battery 162 and/or 172 (Vbat1 and/or Vbat2) to circuitry in the other housing 174 and/or 42. For example, the coil driver 140 and the recharging circuitry 190 in the external charging coil assembly 170 may be powered via Vbat1 (or Vbat1') provided from battery 162 in the external controller/charger 160. This may be sensible because such circuits 140 and 190 may only draw relatively small amounts of power that the relatively-small capacity battery 152 can provide. Likewise, should relatively high-power-draw circuits be resident in the housing 42 of the external controller/charger 160 (such as perhaps the data transmitting amplifier 134), it could be powered by Vbat2 (or Vbat2') from battery 172 in the external charging coil assembly 170.

Although not shown, cable 112 may contain additional wires as necessary to report temperature data from temperature sensor(s) present in the external charging coil assembly 170. Such temperature data may be provided by an analog temperature sensor(s), which reports temperature data to the external controller/charger 160 in analog form, where it is digitized and provided to the microcontroller 130 for interpretation. Alternatively, such analog temperature data may be digitized at the external charging coil assembly 170, or provided directly from a digital thermistor(s) in the assembly 170, and provided to the external controller/charger 160 in digital form—for example via a wire in cable 112 as part of a serial bus interface.

Other examples of circuit implementations for improved integrated external controller/charger systems 150 having external controller/chargers 160 with (smaller capacity) batteries 162 and external charging coil assemblies 170 with (larger capacity) batteries 172 are shown in FIGS. 8B and 8C. In these examples, the coil driver 140 and charging transmitting amplifier 142 are retained in the housing 42 of the external controller/charger 160, as envisioned in FIG. 6. External charging coil assembly 170 may thus lack assembly circuitry 180 altogether, although in FIGS. 8B and 8C recharging circuitry 190 for the battery 172 is retained.

In FIG. 8B, the power supply for the charging transmitting amplifier 142 is coupled to a pin on port 48 on the housing 42 of the external controller/charger 160, with the corresponding pin in connector 114 of the external charging coil assembly 170 coupled to Vbat2 provided by the battery 172. In this way, when the assembly 170 is coupled to the external controller/charger 160, charging transmitting amplifier 142 is powered by the assembly's higher capacity battery 172, allowing battery 162 in the external controller/charger 160 to remain of smaller capacity because it is not drawn upon to produce the magnetic charging field 65 from charging coil 116.

FIG. 8C shows another circuitry variation similar to FIG. 8B, but instead leverages the external controller/charger 160's battery recharging circuitry 194 to provide power needed to produce the magnetic charging field 65 from charging coil 116. In this example, battery 162 in the external controller/charger 160 is rechargeable by the application of DC power to a pin on port 48, with such recharging regulated by the recharging circuitry 194. Typically, such DC power would be provided by an AC-DC converter plugged into a wall outlet as is well known (not shown). When the external charging coil assembly 170 is instead coupled to the port, Vbat2 from the assembly's battery 172 is provided via a pin in connector 114 to the appropriate pin in port 48. Alternatively, if Vbat2 is not of a sufficiently high value to power the battery recharging circuitry 194, it may be boosted to a higher value Vbat2+ by a DC-DC converter 191 in the external charging coil assembly 170, such as a well-known capacitor based charge pump or inductor-base boost converter circuit. In either case, battery 172 will in effect be used to recharge the battery 162 (Vbat1) in the external controller/charger 160. More importantly, because the charging transmitting amplifier 142 is coupled to Vbat1 in this example, this amplifier 142 will be indirectly powered by Vbat2 via the recharge circuitry 194 when the assembly 170 is connected. Hence, and again, the power for producing the magnetic charging field 65 is ultimately supplied by the battery 172 in the external charging coil assembly 170.

Implementation of integrated external controller/charger system 150 is beneficial, regardless of the various manners in which it might be implemented. Because battery 162 in the housing 42 of the external controller/charger 160 is not used to power the charging transmitting amplifier 142 that energizes the charging coil 116, it can be made smaller, as can the housing 42 of the external controller/charger 160. This conveniences patients who normally need to carry their external controller/chargers 160 for immediate IMD control. Inclusion of the battery 172 with the external charging coil assembly 170 may increase the size or thickness of the assembly 170 as compared to the prior art (assembly 110; FIGS. 5A and 5B). But because assembly 170 may only be needed occasionally and not always carried, this inconvenience is mitigated. This is because a patient can generally take care to charge his IMD 10 battery 14 on a schedule—for example, at home or on a daily or weekly basis. Finally, inclusion of the battery 172 with the external charging coil assembly 170 promotes use of the assembly 170 with consumer mobile devices otherwise capable of operating as medical device controllers—such as cell phones—whose internal batteries may not be sufficient to provide the relatively high powers needed for the production of the magnetic charging field 65. This is discussed further later with reference to FIGS. 11A and 11B.

Figure 9A:
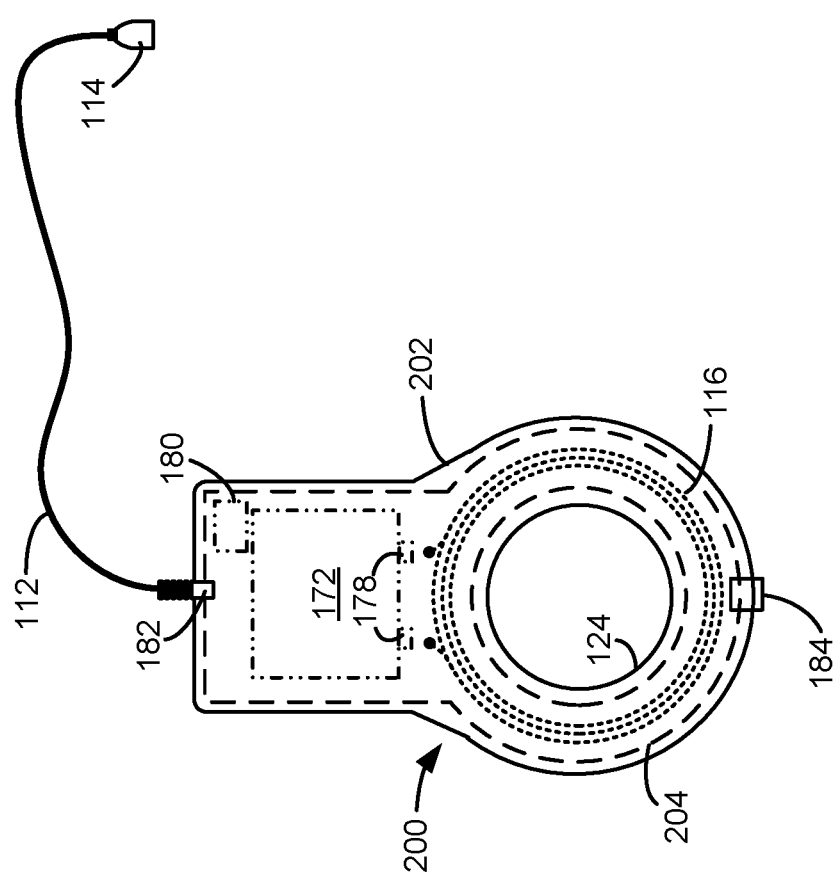

FIGS. 9A and 9B shows different configurations of external charging coil assemblies 200 and 210 which also provide external batteries 172 for providing power to (at least) their charging coils 116. Both of these configurations advantageously move the batteries 172 (and assembly circuitry 180 to the extent present) outside of the area extent of the charging coils 116. This is beneficial to reduce interaction of the magnetic charging field 65 produced by the charging coils 116 with these components. As noted earlier, such interaction can cause unwanted Eddy currents to form, which can generate heat and reduce the efficiency of power transfer. External charging coil assemblies 200 and 210 can implement any of the circuitry approaches of FIGS. 8A-8C discussed earlier.

External charging coil assembly 200 shown in FIG. 9A incorporates the battery 172 in the same housing 202 as the charging coil 116. In this regard, a larger substrate 204 is provided for supporting and electrically coupling the battery 172, the assembly circuitry 180, and the charging coil 116 and the cable termination 182. With the battery 172 moved outside of the charging coil 116, housing 202 may include a hole 124 in the center of the charging coil 116 (compare FIG. 5A). Although not shown, the housing 202 may again include a battery cover (like 188, FIG. 7C) to permit access to the battery 172. A port 184 may again be provided to allow for recharging of the battery 172 in the assembly 200.

External charging coil assembly 210 shown in FIG. 9B incorporates the battery 172 in a different battery housing 212 than the housing 214 for the charging coil 116. The battery housing 212 includes a substrate 216 for supporting and coupling the battery 172, the cable termination 182, and the assembly circuitry 180. Battery housing 212 also includes a port 218 for receiving a connector 220 on the charging coil housing 214. Such coupling as well as passing necessary signals to and from the charging coil 116 (such as from charging transmitting amplifier 142 in the assembly circuitry 180) may also allow the battery housing 212 and the charging coil housing 214 to click together for mechanical robustness, such that such housings will touch to form an integrated battery/coil structure. However, this is not strictly necessary. Instead, a cable 246 (FIG. 10B) may electrically connect components in the battery housing 212 and the charging coil housing 214, thus allowing the housings 212 and 214 to be distant from one other. Note that 218 could alternatively comprise a connector, and 220 a port. Although assembly circuitry 180 is shown on the substrate 216 in the battery housing 212, some or all of such circuitry may instead reside on the substrate 222 in the charging coil housing 214. Again, although not shown, battery housing 212 may include a battery cover for permitting access to the battery 172. Port 218 may be used to recharge the battery 170.

Figure 4:
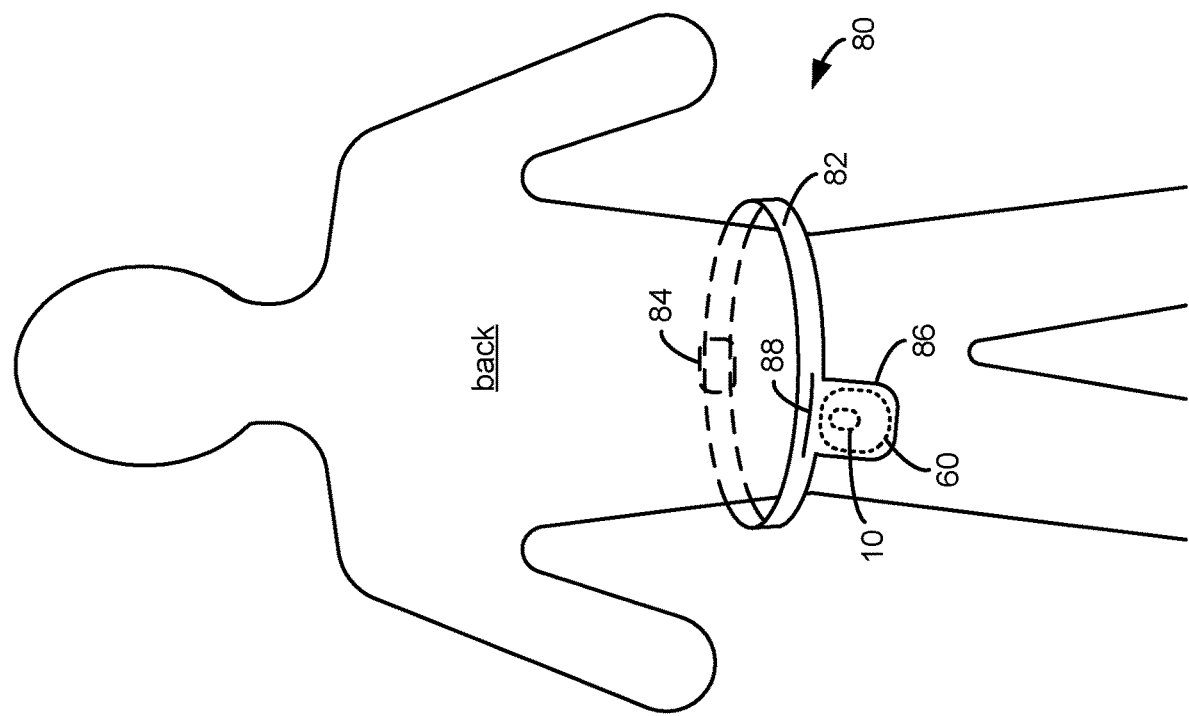
FIG. 4 shows use of a holding device such as a belt to hold an external charger in close proximity to and in alignment with the IMD during a charging session, in accordance with the prior art.

Portions of the various external charging coil assemblies and their associated external batteries 172 can be incorporated into a holding device such as discussed earlier (80; FIG. 4). FIGS. 10A and 10B show different examples. The holding device 230 of FIG. 10A includes a belt 82 with a pouch 232 into which the external charging coil assembly 200 of FIG. 9A is placed. A slot 234 or other opening allows the external charging coil assembly 200 to be inserted into the pouch 232 and to allow its associated cable 112 to exit so that it can be connected to the external controller/charger 160 (FIG. 7A). Slot 234 can be re-sealable (e.g., with Velcro) to allow the external charging coil assembly 200 to be removed so that the holding device 230 can be washed. Alternatively, external charging coil assembly 200 may be permanently enclosed in the pouch 232 during manufacturing, in which case openings (not shown) may be provided in the pouch 232, for example: to allow for exit of the cable 112; to allow access to a battery cover on the housing 202; and/or to allow access to port 184 as needed to recharge battery 172. As before, the pouch 232 will generally align the charging coil 116 with a patient's IMD 10, and once so aligned the patient may then couple connector 114 to his external controller/charger 160 (FIG. 7A) and use its GUI to begin a charging session—i.e., to produce magnetic charging field 65 to charge the battery 14 in his IMD 10. The external charging coil assembly 210 of FIG. 9B may also be positioned within pouch 232, although this is not shown.

The holding device 240 of FIG. 10B includes a belt 82 with pouches 242 and 244 into which the charging coil housing 214 and the battery housing 212 of the external charging coil assembly 210 of FIG. 9B are respectively placed. In this example, the charging coil housing 214 and the battery housing 212 are not directly mechanically coupled at connector 220 and port 218 as shown in FIG. 9B. Instead, a cable 246 couples to 220 and 218 to electrically couple the components in the housings 214 and 212. Cable 246 is preferably internal to the belt 82 and spans between pouches 242 and 244 as assisted by openings 248. This configuration allows the charging coil housing 214 and the battery housing 212 to be positioned at different locations on the belt. Such positioning is beneficial: the charging coil housing 214 is at the back of the belt 82 proximate to the location of IMD implantation in the patient (in an SCS application); the battery housing 212 by contrast is at the front of the belt 82, where cable 112 exits pouch 244. This makes coupling of the battery housing 212 (and the charging coil housing 214) to the external controller/charger 160 easier, because cable 112/connector 114 are in front of the patient and easier to reach. While electrical components of the belt 82 may be removable, such components may also be permanently integrated into the holding device 240. Note also that cable 246 may be hardwired to and not detachable from the charging coil housing 214 and the battery housing 212.

Figure 11A:
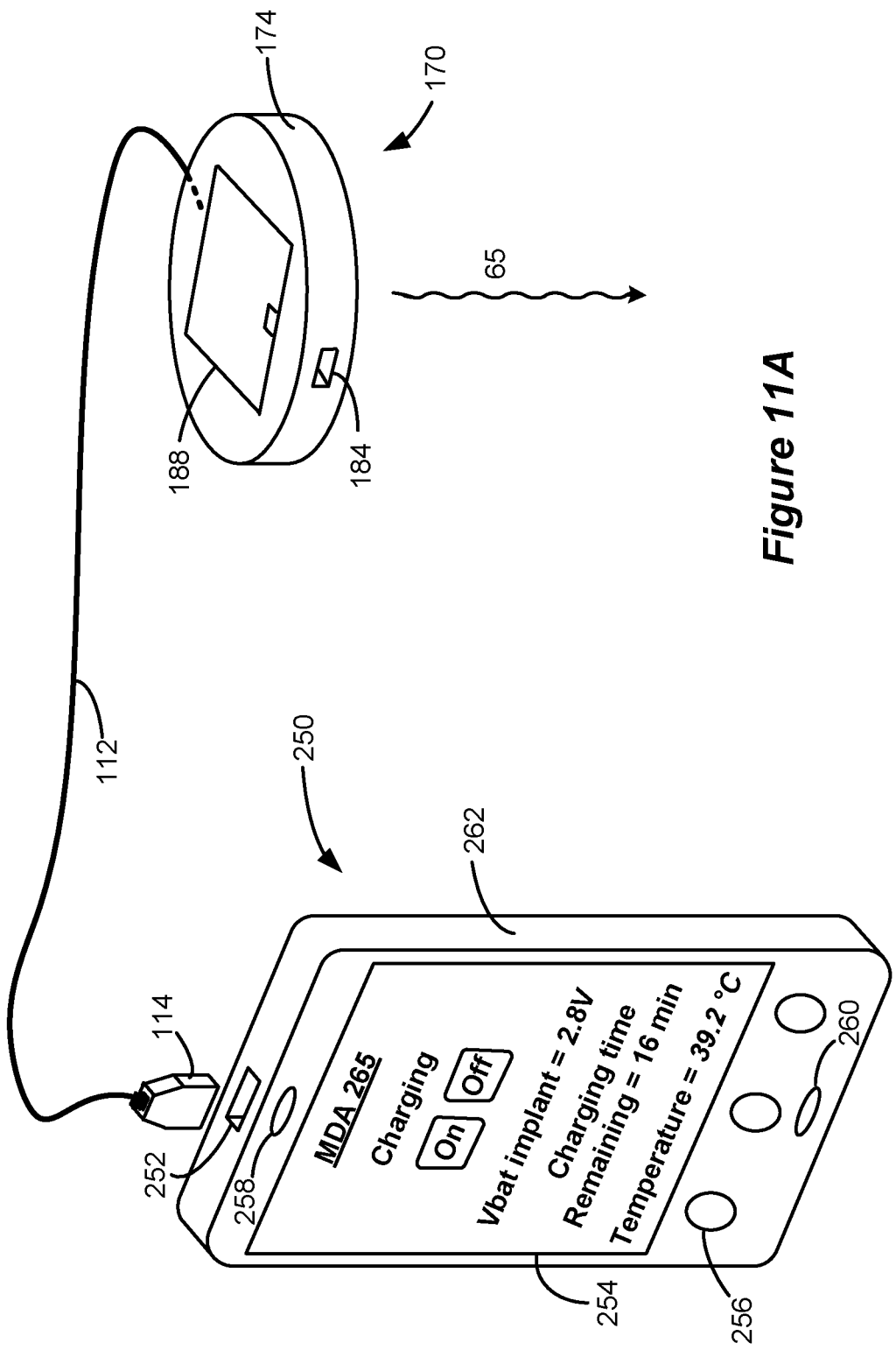
FIGS. 11A and 11B show other mobile devices operable as the external controller/charger and useable with the disclosed external charging coils assemblies, in accordance with examples of the invention.
Figure 11B:
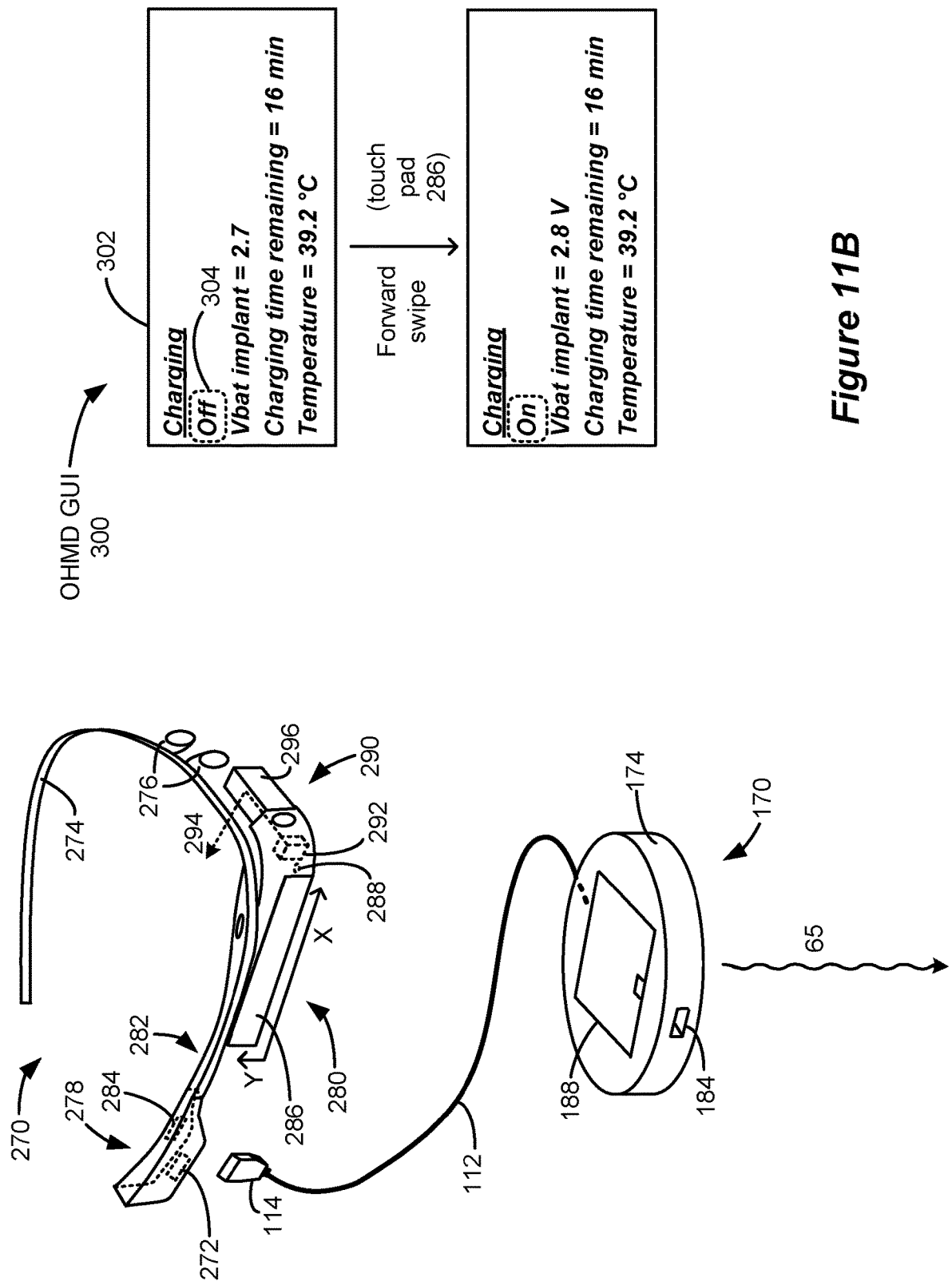

As noted earlier, consumer mobile devices have been disclosed in the art as suitable for use as data-communicating external controllers for IMDs. As noted, the batteries present in typical mobile devices may have insufficient capacities to additionally allow a mobile device to act as an external charging device for an IMD. However, the disclosed external charging coil assemblies and their associated external batteries 172 enable such charging functionality, and FIGS. 11A and 11B illustrate different types of mobile devices useable as external controller/chargers with the disclosed assemblies. External charging coil assembly 170 with its internal battery 172 (FIGS. 7A-7C) is shown in these examples, although other disclosed assemblies (FIG. 9A, 200; FIG. 9B, 210) could be used as well. The disclosed external charging coil assemblies useable with the illustrated mobile devices could also be held by or integrated with the holding devices illustrated earlier with respect to FIGS. 10A and 10B, although this isn't shown in FIGS. 11A and 11B.

FIG. 11A shows use of cell phone mobile device 250 as an external controller/charger, and coupled to external charging coil assembly 170 at a port 252 (e.g., a USB port) that are typically present on such devices. The cell phone 250 may be a commercial, multipurpose, consumer device, such as a cell phone, tablet, personal data assistant, laptop or notebook computer, or like device—essentially any mobile, hand-holdable device capable of functioning as a wireless external controller for an IMD. Examples include the Apple iPhone or iPad, Microsoft Surface, Nokia Lumia devices, Samsung Galaxy devices, and Google Android devices for example. FIG. 11A in particular illustrates the cell phone 250 as a smart cellular phone. Port 252 on cell phone 250 can comprise different types of ports beyond USB ports.

Figure 11C:
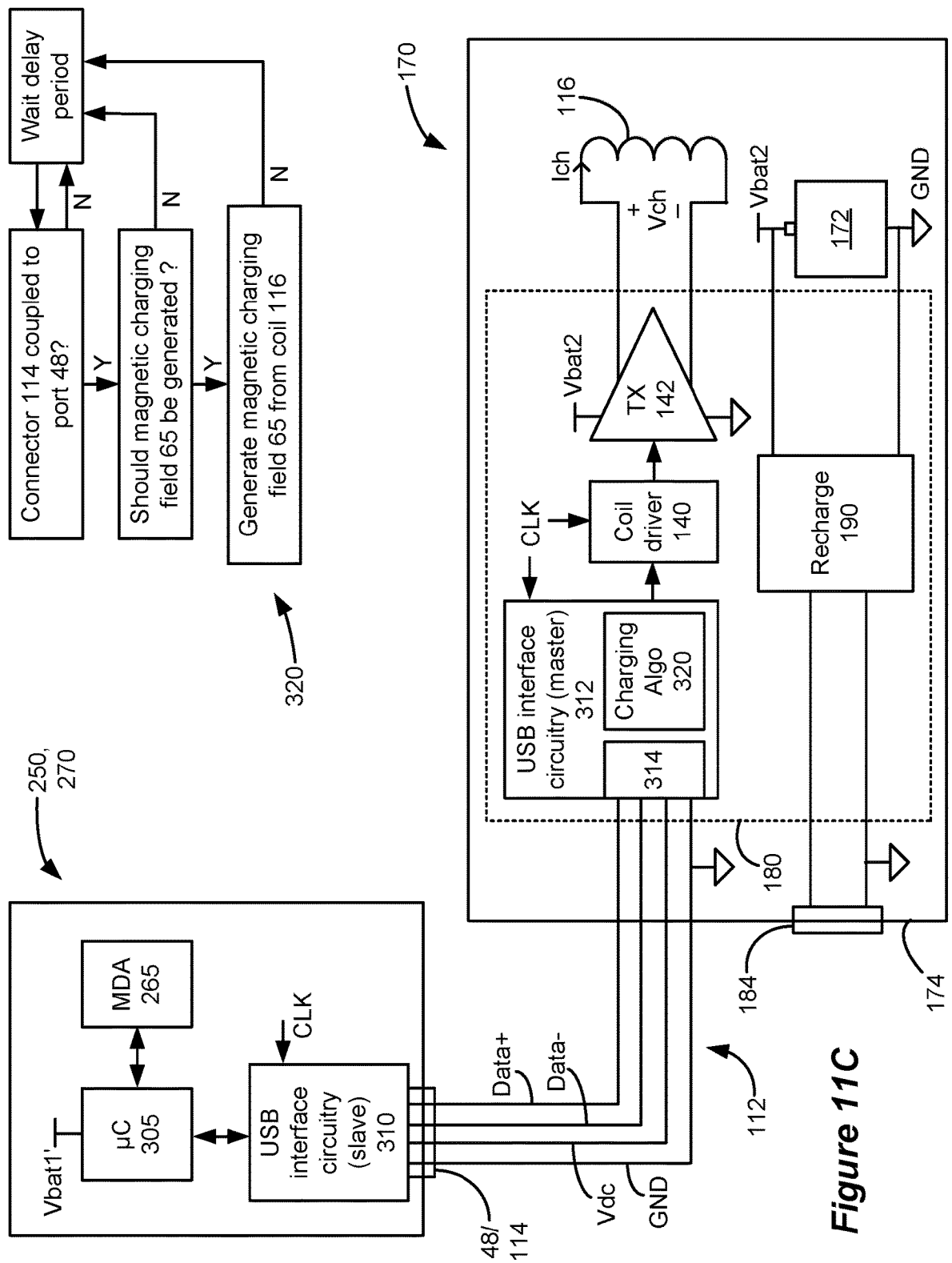
FIG. 11C shows circuitry operable in the mobile devices and external charging coils assemblies of FIGS. 11A and 11B.

The cell phone 250 includes a GUI with a screen 254, which may also receive input if it is a touch screen. The cell phone 250 may also have buttons 256 (e.g., a keyboard) for receiving input from the patient, a speaker 258, and a microphone 260. Although not shown, cell phone 250 further includes within its housing 262: a battery (primary or rechargeable); an antenna; and a microcontroller 305 (FIG. 11C). As mentioned earlier, cell phone 250's microcontroller 305 can execute a Medical Device Application (MDA) 265 to enable data communications with the IMD 10—i.e., to control IMD operation and to monitor IMD function. Such communications can occur using the cell phone 250's antenna, as explained in the references cited herein.

The MDA 265, like other applications selectable in the cell phone 250, may have been downloaded to the cell phone 250 using traditional techniques, such as from an Internet server or an "app store." Although not strictly necessary, MDA 265 is logically developed and provided by the manufacturer of the IMD 10, and may be made available in different versions to work with different mobile device operating systems (e.g., iOS, Android, Windows, etc.). One skilled in the art will understand that MDA 265 comprises instructions that can be stored in the cell phone 250 or on an Internet server for example on non-transitory machine-readable media, such as magnetic, optical, or solid-state discs, integrated circuits, memory sticks, tapes, etc.

MDA 265 is modified to provide GUI elements relevant to IMD charging, and FIG. 11A shows an example of a charging GUI on screen 254. The charging GUI may have been navigated to by the patient by making appropriate selections in the MDA 265. Alternatively, charging GUI may be rendered automatically upon insertion of the external charging coil assembly 170's connector 114 into port 252. As shown, charging GUI includes patient-selectable on-screen buttons to turn charging on or off. Additionally, charging GUI can include information relevant to the current or future charging session, such as the current voltage of the IMD 10's battery 14; an estimation of the (remaining) charging time; and a temperature. Such information can be periodically updated via telemetry from the IMD 10 to the cell phone 250, and if a charging session is underway and a magnetic charging field 65 generated, possibly by LSK telemetry, as described earlier. Temperature information may come from measurements taken at the IMD 10 (by IMD temperature sensors) and telemetered, or may come from temperature measurements made by temperature sensors present in the external charging coil assembly 175.

FIG. 11B shows use of a wearable mobile device, specifically an Optical Head-Mounted Display (OHMD) 270, as an external controller/charger 250, and coupled to external charging coil assembly 170 at a port 272 (e.g., a USB port). More specifically, OHMD 270 can in one example comprise the Google Glass™ OHMD, developed by Google, Inc. of Mountain View, Calif. As described further in U.S. Patent Application Publication 2015/0360038, OHMD 270 is configured to be wearable much like a pair of standard eyeglasses, and includes a frame 274 which also serves as the temples supported by the wearer's ears, and nose pads 276. Lenses (e.g., corrective or sunglasses lenses) may be affixed to the frame 274, but are not shown in FIG. 11B. OHMD 270 may also be worn in conjunction with a wearer's normal eyeglasses.

Plastic affixed to the frame 274 generally defines a rearward housing 278 and a forward housing 280 on the OHMD 270's right temple. Plastic also defines a pass-through portion 282, which as well as defining a space for the wearer's right ear, also provides for the passing of wires between the two housings 278 and 280. The rearward housing 278 holds a rechargeable battery (not shown). A bone-conduction audio transducer 284 in the rearward housing 278 protrudes through the plastic and presses over the right ear to permit the wearer to hear sounds provided by the OHMD's GUI, which is explained below. OHMD 270 could also include a more-traditional audio speaker as well.

The forward housing 280 includes a printed circuit board (not shown), which supports the OHMD 270's main electronics, such as its microcontroller 305, and movement sensors providing input to a motion detector module in the electronics, including a three-axis accelerometer and a three-axis gyroscope. Also included in the forward housing 280 is a touch sensor (not shown), which allows the outer surface of the forward housing to operate as a touch pad 286. The touch pad 286 is sensitive to the wearer's touch across the two-dimensional expanse (X and Y) of the outer surface of the foreword housing 280, and can additionally be pressed ("tapped") similar to a button. The underside of the forward housing 280 additionally includes a microphone 288 for the receipt of voice input in addition to inputs receivable by the touch pad 286. The electronics of the OHMD 270 will include a voice detection module for interpretation of spoken voice inputs, as is well known.

The forward housing 280 also includes a display portion 290 of the OHMD 270, including an LED array 292 powered by the OHMD's microprocessor 305. Images 294 created at the LED array 292 are directed to a prism 296 containing a polarizing beam-splitter that direct the images 294 to the wearer's right eye. In this manner, the user is able to perceive the images 294 generated by the OHMD 270 and output by the display portion 290, which images 294 are provided slightly to the right of the wearer's center of vision, thus allowing the wearer to see the real world and the images on the display portion 290 simultaneously.

OHMD 270 in this example further includes bi-directional short-range RF communication means, which like the cell phone 250 described earlier (FIG. 11A) preferably includes one or more antennas (not shown) compliant with Bluetooth and Wi-Fi communication standards. The antenna may be located in the forward housing 280, but could be present elsewhere, such as in the rearward housing 278.

As explained in the '038 Publication, the OHMD 270 can generate a GUI 300 using the display portion 290 that can be used to control and monitor the IMD 10. The input interface of the GUI 300 comprises one or more of the touch pad 286, the voice detection module (coupled to microphone 288), and the motion detector module coupled to the accelerometers and gyroscopes. This input interface allows a patient to navigate the GUI 300 to control and monitor his IMD 10 either by touch, voice, or head movements. Audio aspects (e.g., transducer 284 or another speaker) can also comprise part of the OHMD GUI 300.

The '038 Publication explains the OHMD GUI 300 in detail, in particular as relevant to data communications with the IMD. However, only a simple example of OHMD 300 as relevant to charging is shown in FIG. 11B. Again, the charging aspects of GUI 300 may have been navigated to by the patient using the input interface of the OHMD 270, or rendered automatically upon insertion of the external charging coil assembly 170's connector 114 into port 272. As seen by the patient via the display portion 290, a card 302 of information regarding to IMD battery charging is shown, which is similar to the charging GUI of the cell phone 250 discussed in FIG. 11A, and thus not repeated. A cursor 304 highlights a selection option, and in card 302 is associated with turning charging—production of the magnetic charging field 65 via external charging coil assembly 170—on or off. Other information relevant to a current or future charging session may also be displayed as before. In the example shown, charging is currently off, but is turned on by swiping forward on the touch pad 286, which then updates the on/off information on the displayed card. However, other user inputs to input interface—such as voice commands or head movements, may also be used to navigate the OHM GUI 300 and to make user selections.

Note that different external charging coil assemblies and their associated external batteries 172 can be used in the various examples of improved external controller/charger system 100. For example, as disclosed in U.S. Pat. No. 8,682,444, an external charger device can be coupled to external charging coils of different shapes and sizes, with the external charger programmed to automatically detect a particular one of the external charging coils and to adjust generation of the magnetic charging field 65 accordingly (e.g., its power). Similar programming of the disclosed external controller/charger 160, cell phone 250, or OHMD 270, would permit use of this technology, thus enabling such devices to change magnetic field generation based upon the particular external charging coil assembly used.

Further details regarding use of a mobile device 250, 270 as a controller for the various disclosed external charging coil assemblies are shown in the circuitry of FIG. 11C. Such circuitry is practical to consider in an actual implementation, because mobile device 250, 270 may be programmed via its USB interface circuitry 310 to operate as a slave with respect to USB communication at its port 48. Use of slave USB interface circuitry 310 in mobile device 250, 270 allows the device to be controlled by another computer device, such as a personal computer, which operates as a master to control USB communications at port 48.

In recognition of the possible nature of the mobile device 250, 270 as a USB slave, the external charging coil assembly (e.g., 170) preferably includes programmable USB interface circuitry 312 operating as a master. Master USB interface circuitry 312 in the external charging coil assembly 170 controls communications on cable 112 when connector 114 is connected to port 48 on mobile device 250, 270, and further controls generation of the magnetic charging field 65 from charging coil 116 depending on such communications.

Such operation can occur via a charging algorithm 320 programmed into the master USB interface circuitry 312, which operation is described in the flow chart at the top of FIG. 11C. Algorithm 320 preferably operates continuously with a delay period, such as 0.5 seconds or so. After expiration of the delay period, algorithm 320 determines whether the connector 114 of the external charging coil assembly 170 has been connected to a USB port, such as port 48 on the mobile device 250, 270. This can occur using well-known connection detection circuitry 314 in the external charging coil assembly 170.

If connected, the master USB interface circuitry 312 determines whether it should control the coil driver 140 to produce a magnetic charging field 65 from the charging coil 116. This can occur by master USB interface circuitry 312 sending an inquiry to the mobile device 250, 270 along data signals Data+ and Data− in the cable 112. Such data signals are differential in accordance with the USB protocol supported by circuitries 310 and 312, as is well known. For example, master USB interface circuitry 312 may inquire as to the status of the MDA 265 operating in the mobile device 250, 270. If the MDA 265 indicates that a magnetic charging field 65 should be generated—for example, if the patient has selected the "on" charging button on the mobile device 150, 270 GUIs—the slave USB interface circuitry 310 can inform the master USB interface circuitry 312 of this fact. In turn, the master USB interface circuitry 312 can control the coil driver 140 to energize the transmitting charging amplifier 142, thus producing the magnetic charging field 65. Whether magnetic charging field 65 generation should continue can be determined periodically—for example, by inquiring after successive delay periods whether MDA 265 later indicates that the field should cease. In short, charging algorithm 320 operating with the USB interface circuitry 312 controls communications with port 48 on the mobile device 250, 270 to receive information concerning the need to start or stop charging depending on the status of the MDA 265.

Although shown separately from control circuitry in FIG. 11C, it should be understood that USB interface circuitry 310 and 312 can be programmed into control circuitry (e.g., 305) otherwise operable in the devices. Although illustrated in the context of USB communications, other communication protocols may be used for mobile device 250, 270/external charging coil assembly 170 communications.

Although disclosed for use with an implantable medical device, it should be understood that the various examples of external controller/chargers and external charging coil assemblies and their associated batteries may be used with other non-implantable medical devices as well. For example, the disclosed external systems may be used in conjunction with an External Trial Stimulator (ETS) device used to mimic operation of the IMD 10 prior to its implantation, as disclosed for example in U.S. Pat. No. 9,327,135, and U.S. Patent Application Publication 2012/0123502, which are incorporated herein by reference.

Microcontroller control circuitry operable in the IMD 10, external controller charger/controller 160, mobile device 250 or 270 can comprise for example Part Number MSP430, manufactured by Texas Instruments, which is described in data sheets at http://www.ti.com/lsds/ti/microcontroller/16-bit_msp430/overview.page? DCMP=MCU_other& HQS=msp430, which is incorporated herein by reference. However, other types of control circuitry may be used in lieu of a microcontroller as well, such as microprocessors, FPGAs, DSPs, or combinations of these, etc.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system for use with a medical device, comprising:
   an external controller, comprising
   a first housing with a first port,
   at least one antenna for communicating data with the medical device, and
   a first battery;
   a charging coil assembly for use with a medical device, comprising
   a first connector configured to couple to the first port,
   a charging coil configured to produce a magnetic charging field for the medical device, wherein production of the magnetic charging field is controlled by the external controller via the first connector, and
   a second battery; and
   first circuitry powered by the second battery, wherein the first circuitry is configured to energize the charging coil to produce the magnetic charging field.

2. The system of claim 1, wherein the at least one antenna comprises at least one coil antenna, and wherein the at least one coil antenna communicates data with the medical device via magnetic inductive coupling.

3. The system of claim 1, wherein the at least one antenna communicates data with the medical device via short-range electromagnetic RF telemetry.

4. The system of claim 1, wherein the at least one antenna communicates data with the medical device to monitor and/or control the medical device.

5. The system of claim 1, further comprising a second housing and a third housing, wherein the charging coil is within the second housing, the second battery is within the third housing, and the first and second housings are electrically coupled.

6. The system of claim 5, further comprising a holding device configured to be wearable by a medical device patient, wherein the holding device is configured when worn by the patient to hold the second housing proximate to the medical device of the patient.

7. The system of claim 6, wherein the first and second housings are located at different positions on the holding device, and wherein the second and third housings are electrically coupled by a cable within the holding device.

8. The system of claim 1, further comprising a second housing, wherein the charging coil and the second battery are within the housing.

9. The system of claim 1, wherein the external controller contains a user interface configured to receive an input from a user, and wherein the charging coil assembly does not contain a user interface configured to receive an input from a user.

10. The system of claim 9, wherein the user interface is configured to allow a user to communicate the data with the medical device, and to control production of the magnetic charging field from the charging coil.

11. The system of claim 1, wherein the first circuitry is within the first housing, and wherein the first connector comprises a first signal to send a first voltage provided or generated from the second battery to the first circuitry, and second signals coupled to ends of the charging coil.

12. The system of claim 11, wherein the external controller further comprises battery recharging circuitry for the first battery, and wherein the first voltage is coupled to a pin on the first connector corresponding with a pin of the first port meeting with the battery recharging circuitry.

13. The system of claim 1, wherein the first circuitry comprises an amplifier.

14. The system of claim 1, wherein the charging coil assembly further comprises at least one temperature sensor, wherein a temperature determined by the at least one temperature sensor is reported to the external controller via the first connector and the first port.

15. The system of claim 1, wherein the first connector is attachable to and detachable from the first port of the external controller.

16. The system of claim 1, wherein the second battery only powers the first circuitry.

17. The system of claim 1, wherein the second battery does not power circuitry in the external controller.

18. The system of claim 1, wherein the charging coil assembly further comprises communication interface circuitry coupled to the first connector, wherein the communication interface circuitry is configured to control communications with the first port of the external controller.

19. The system of claim 1, wherein the external controller comprises a cell phone.

20. A system for use with a medical device, comprising:
a non-transitory machine-readable medium upon which are stored instructions for a medical device application executable by a mobile device, wherein the medical device application when executed on the mobile device is configured to:
provide a Graphical User Interface (GUI) on the mobile device to allow a user to communicate data between the mobile device and a medical device, and to control charging of the medical device; and
a charging coil assembly, comprising:
a first connector configured to couple to a first port of a mobile device executing the medical device application;
a charging coil configured to produce a magnetic charging field for the medical device, wherein production of the magnetic charging field is controlled by GUI; and
a battery, wherein the battery is configured to power first circuitry to energize the charging coil to produce the magnetic charging field.

* * * * *